US009650364B2

(12) United States Patent
Casillas et al.

(10) Patent No.: US 9,650,364 B2
(45) Date of Patent: May 16, 2017

(54) QUINAZOLINES AS KINASE INHIBITORS

(71) Applicant: GlaxoSmithKline Intellectual Property Development Limited, Brentford, Middlesex (GB)

(72) Inventors: Linda N. Casillas, Collegeville, PA (US); Adam Kenneth Charnley, Collegeville, PA (US); Xiaoyang Dong, Collegeville, PA (US); Pamela A. Haile, Collegeville, PA (US); Michael P. Demartino, King of Prussia, PA (US); John F. Mehlmann, Collegeville, PA (US)

(73) Assignee: GlaxoSmithKline Intellectual Property Development Limted (GB)

( * ) Notice: Subject to any disclaimer, the term of this patent is extended or adjusted under 35 U.S.C. 154(b) by 0 days.

(21) Appl. No.: 14/762,905

(22) PCT Filed: Feb. 19, 2014

(86) PCT No.: PCT/IB2014/059094
§ 371 (c)(1),
(2) Date: Jul. 23, 2015

(87) PCT Pub. No.: WO2014/128622
PCT Pub. Date: Aug. 28, 2014

(65) Prior Publication Data
US 2015/0361069 A1    Dec. 17, 2015

Related U.S. Application Data

(60) Provisional application No. 61/767,423, filed on Feb. 21, 2013.

(51) Int. Cl.
*C07D 403/12* (2006.01)
*C07D 405/14* (2006.01)
*A61K 9/20* (2006.01)
*A61K 9/48* (2006.01)

(52) U.S. Cl.
CPC .......... *C07D 403/12* (2013.01); *A61K 9/2054* (2013.01); *A61K 9/4866* (2013.01); *C07D 405/14* (2013.01)

(58) Field of Classification Search
CPC .................................................. C07D 401/04
See application file for complete search history.

(56) References Cited

U.S. PATENT DOCUMENTS

| | | | |
|---|---|---|---|
| 4,916,135 A | 4/1990 | Effland et al. ............... 514/254 |
| 5,457,105 A | 10/1995 | Barker ....................... 514/234.5 |
| 5,576,322 A | 11/1996 | Takase et al. |
| 5,710,158 A | 1/1998 | Myers et al. ................ 514/259 |
| 5,747,498 A | 5/1998 | Schnur et al. |
| 5,801,180 A | 9/1998 | Takase et al. |
| 6,046,206 A | 4/2000 | Pamukcu et al. ............ 514/259 |
| 6,548,508 B2 | 4/2003 | Westbrook et al. |
| 6,589,758 B1 | 7/2003 | Zhu ............................... 435/15 |
| 6,743,799 B2 | 6/2004 | Westbrook et al. |
| 6,809,097 B1 | 10/2004 | Thomas et al. ............ 514/235.2 |
| 7,282,504 B2 | 10/2007 | Armistead et al. .......... 514/275 |
| 7,452,887 B2 | 11/2008 | Dickson, Jr. et al. ... 514/253.06 |
| 7,566,786 B2 | 7/2009 | Baldwin et al. ............. 546/159 |
| 7,569,577 B2 | 8/2009 | Hennequin et al. ..... 514/266.22 |
| 7,618,975 B2 | 11/2009 | Cai et al. ................... 514/262.1 |
| 7,709,479 B1 | 5/2010 | Mortlock et al. .......... 514/235.8 |
| 7,939,546 B2 | 5/2011 | Phiasivongsa et al. ...... 514/313 |
| 8,258,145 B2 | 9/2012 | Cai et al. ................. 514/266.21 |
| 9,216,965 B2 | 12/2015 | Casillas et al. |
| 2002/0026052 A1 | 2/2002 | Boschelli et al. ............ 546/122 |
| 2002/0147214 A1 | 10/2002 | Cockerill et al. ............ 514/311 |
| 2003/0087919 A1 | 5/2003 | Nagarathnam et al. |
| 2003/0105129 A1 | 6/2003 | Mortlock et al. ............ 514/313 |
| 2003/0125344 A1 | 7/2003 | Nagarathnam et al. |
| 2003/0212276 A1 | 11/2003 | Boschelli et al. ............ 546/153 |
| 2003/0216417 A1 | 11/2003 | Cumming .................. 514/266.4 |
| 2003/0220357 A1 | 11/2003 | Bankston et al. |
| 2004/0242604 A1 | 12/2004 | Bhattacharya et al. ... 514/266.4 |
| 2005/0070561 A1 | 3/2005 | Jung et al. ............... 514/266.23 |
| 2005/0137395 A1 | 6/2005 | Hong et al. .................. 540/575 |
| 2005/0267101 A1 | 12/2005 | Randle ......................... 514/221 |
| 2006/0025327 A1 | 2/2006 | Sanchez et al. ................. 514/2 |
| 2006/0116357 A1 | 6/2006 | Heron et al. .................... 514/80 |
| 2006/0167035 A1 | 7/2006 | Schwede et al. ............. 514/291 |
| 2007/0021446 A1 | 1/2007 | Ehlert et al. ............... 514/266.2 |
| 2007/0299092 A1 | 12/2007 | Floyd, Jr. et al. ......... 514/266.1 |
| 2008/0032996 A1 | 2/2008 | Mitsuya et al. .......... 514/255.05 |
| 2008/0045568 A1 | 2/2008 | Deng et al. .................. 514/312 |
| 2008/0064878 A1 | 3/2008 | Aoki et al. ................. 546/277.4 |
| 2008/0161305 A1 | 7/2008 | Forsyth et al. ............ 514/235.2 |
| 2008/0221132 A1 | 9/2008 | Cai et al. ................. 514/263.24 |
| 2008/0227811 A1 | 9/2008 | Chen ............................ 514/312 |
| 2008/0227812 A1 | 9/2008 | Chen ............................ 514/313 |
| 2008/0234267 A1 | 9/2008 | Lackey ...................... 514/235.2 |
| 2008/0269404 A1 | 10/2008 | Paul et al. .................... 524/558 |
| 2008/0312273 A1 | 12/2008 | Hennequin .................. 514/311 |
| 2008/0318971 A1 | 12/2008 | Hewes ...................... 514/252.18 |
| 2009/0099106 A1 | 4/2009 | Phiasivongsa et al. ........ 514/43 |
| 2009/0215770 A1 | 8/2009 | Jung et al. |
| 2009/0226443 A1 | 9/2009 | Filvaroff et al. |
| 2009/0270450 A1 | 10/2009 | Dakin et al. ................. 514/313 |
| 2010/0069412 A1 | 3/2010 | Heron et al. |
| 2010/0135999 A1 | 6/2010 | Nazare et al. ............. 424/133.1 |
| 2011/0053935 A1 | 3/2011 | Folkes et al. .............. 514/235.2 |
| 2011/0237629 A1 | 9/2011 | Meibom et al. ............. 514/340 |
| 2011/0256092 A1 | 10/2011 | Phiasivongsa et al. ..... 424/85.2 |

(Continued)

FOREIGN PATENT DOCUMENTS

CN    101362719 A    2/2009
EP    0 973 746 B1    9/2003
(Continued)

OTHER PUBLICATIONS

Sheth, et al. Archives of Biochemistry and Biophysics, 503: 191-201 (Aug. 10, 2010).

(Continued)

*Primary Examiner* — Paul V Ward
(74) *Attorney, Agent, or Firm* — Fang Qian; Edward R. Gimmi; William R. Majarian

(57) ABSTRACT

Disclosed are compounds that are inhibitors of RIP2 kinase and methods of making and using the same.

17 Claims, 2 Drawing Sheets

(56) References Cited

U.S. PATENT DOCUMENTS

| | | | |
|---|---|---|---|
| 2011/0262436 A1 | 10/2011 | Bender et al. | |
| 2012/0041024 A1 | 2/2012 | Charnley et al. | 514/313 |
| 2012/0053183 A1 | 3/2012 | Russu et al. | |
| 2012/0070413 A1 | 3/2012 | Kim et al. | 424/85.4 |
| 2012/0122923 A1 | 5/2012 | Cosledan et al. | 514/313 |
| 2012/0165321 A1 | 6/2012 | Adams et al. | 514/223.2 |
| 2012/0219522 A1 | 8/2012 | Xi | 424/85.4 |
| 2013/0018039 A1 | 1/2013 | Bodmer et al. | 514/210.21 |
| 2013/0023532 A1 | 1/2013 | Casillas et al. | 514/234.2 |
| 2013/0023534 A1 | 1/2013 | Casillas et al. | 514/236.5 |
| 2013/0053375 A1 | 2/2013 | Bury et al. | 514/228.2 |
| 2013/0345258 A1 | 12/2013 | Bury et al. | 514/313 |
| 2014/0100234 A1 | 4/2014 | Knight et al. | 514/252.04 |
| 2014/0155396 A1 | 6/2014 | Bannen et al. | 514/234.5 |
| 2014/0256949 A1 | 9/2014 | Casillas et al. | |

FOREIGN PATENT DOCUMENTS

| | | | |
|---|---|---|---|
| EP | 2 072 502 A1 | 6/2009 | |
| GB | 2 345 486 A | 7/2000 | |
| WO | WO 95/15758 A1 | 6/1995 | |
| WO | WO 96/09294 A1 | 3/1996 | |
| WO | WO 98/05647 A1 | 2/1998 | |
| WO | WO 99/35146 A1 | 7/1999 | |
| WO | WO 02/068394 A1 | 9/2002 | |
| WO | WO 02/092571 A1 | 11/2002 | |
| WO | WO 03/018022 A1 | 3/2003 | |
| WO | WO 03/026666 A1 | 4/2003 | |
| WO | WO 03/055491 A1 | 7/2003 | |
| WO | WO 2004/037814 A1 | 5/2004 | |
| WO | WO 2004/058781 A1 | 7/2004 | |
| WO | WO 2007/045987 A1 | 4/2007 | |
| WO | WO 2008/033748 A2 | 3/2008 | |
| WO | WO 2008/033749 A2 | 3/2008 | |
| WO | WO 2008/119771 A2 | 10/2008 | |
| WO | WO 2009/080200 A1 | 7/2009 | |
| WO | WO 2011/011522 A2 | 1/2011 | |
| WO | WO 2011/112588 A1 | 9/2011 | |
| WO | WO 2011/120025 A1 | 9/2011 | |
| WO | WO 2011/120026 A1 | 9/2011 | |
| WO | WO 2011/123609 A1 | 10/2011 | |
| WO | WO 2011/140442 A1 | 11/2011 | |
| WO | WO 2012/021580 A1 | 2/2012 | |
| WO | WO 2012/122011 A2 | 9/2012 | |
| WO | WO 2013/025958 A1 | 2/2013 | |
| WO | WO 2014/043437 A1 | 3/2014 | |
| WO | WO 2014/043446 A1 | 3/2014 | |
| WO | WO 2014/128622 | 8/2014 | |
| WO | WO 2014/128622 A1 | 8/2014 | |

OTHER PUBLICATIONS

Cavasotto, et al. Bioorg. & Med. Chem. Lett., 16: 1969-1974 (2006).
Kumar, et al. J. Clin. Oncol., 26: 1742-1751 (Apr. 1, 2008).
Manon, et al. J. Molec. Biol., 365: 160-174 (2007).
Robinett, et al. Bioorg. Med. Chem. Lett., 17: 5886-5893 (2007).
Argast, et al. Molec. & Cell. Biochem., (Kluwer Academic Pubs) 268(1-2): 129-140 (2005).
PCT International Preliminary Report on Patentability & PCT Written Opinion of the International Searching Authority, PCT/US11/35521, Aug. 9, 2011.
PCT International Preliminary Report on Patentability & PCT Written Opinion of the International Searching Authority, PCT/US11/47183, Dec. 30, 2011.
PCT International Preliminary Report on Patentability & PCT Written Opinion of the International Searching Authority, PCT/US12/27439, Jun. 7, 2012.
PCT International Preliminary Report on Patentability & PCT Written Opinion of the International Searching Authority, PCT/US12/51247, Oct. 23, 2012.
PCT International Preliminary Report on Patentability & PCT Written Opinion of the International Searching Authority, PCT/US13/59600, Jan. 29, 2014.
PCT International Preliminary Report on Patentability & PCT Written Opinion of the International Searching Authority, PCT/US13/59619, Jan. 29, 2014.
EP Supplementary Search Report for PCT/US11/030103, dated Sep. 23, 2013.
EP Supplementary Search Report for PCT/US11/030104, dated Sep. 17, 2013.
EP Supplementary Search Report for PCT/US11/35521, dated Oct. 23, 2013.
EP Supplementary Search Report for PCT/US11/47183, dated Dec. 17, 2013.
Amendment, U.S. Appl. No. 14/239,193, filed on May 12, 2015.
Tigno-Aranjuez, Genes & Development, vol. 24, 2666-2677 (2010).
Cai, et al. Journal of Medicinal Chemistry, 53(5): 2000-2009 (2010).
EP Supplementary Search Report for PCT/US2012/027439, dated Dec. 16, 2014.
Amendment, U.S. Appl. No. 14/283,352, filed Apr. 7, 2015.
Amendment, U.S. Appl. No. 14/396,559, filed Apr. 7, 2015.
Amendment, U.S. Appl. No. 14/002,147, filed May 15, 2015.
Amendment, U.S. Appl. No. 13/696,603, filed on Feb. 6, 2015.
Foley et al., Pediatric Rheumatology, 2013,11 (Suppl):A3 (published Nov. 8, 2013; presented 7th Congress of ISSAID, Lusanne, Switzerland May 22-26, 2013).
Poster: C.R. Hanning, AAI Annual Meeting, Pittsburgh PA (May 4, 2014).
Poster: B. J. Votta, et al., Keystone Symposia on Innate Immunity, Keystone, CO (Mar. 7, 2012).
EP Supplementary Search Report for PCT/US2012/051247,dated Feb. 18, 2015.
Arostegui, et al., Arthritis & Rheumatism, 56(11):3805-3813 (2007).
Biancheri, et al., Digestive and Liver Disease, Abstract, 45S:S71 (2013).
Body-Malapel, et al., Laboratory Investigation, 88:318-327 (2008).
Carreno, et al., Acta Ophthalmologica, Abstract, 2014.
Corridoni, et al., PNAS, 110(42):16999-17004 (2013).
Denou, et al., EMBO Molecular Medicine, 7(3):259-274 (2015).
Dharancy, et al., Gastroenterology, 138:1546-1556 (2010).
Du, et al., Kidney International, 84:265-276 (2013).
Ermann, et al., PNAS, E2559-E2566 (2014).
Ferrero-Miliani, et al., Clinical and Experimental Immunology, 147:227-235 (2006).
Foley, et al., Pediatric Rheumatology, 11 (Suppl. 1):A3 (2013).
Geddes, et al., Infection and Immunity, 78(12):5107-5115 (2010).
Goh, et al., The Journal of Immunology, 191:2691-2699 (2013).
Goncalves, et al., The Scandanavian Journal of Immunology, 73:428-435 (2011).
Hedegaard, et al., Plos One, 6(5):e20253 (2011).
Heinhuis, et al., Ann Rheum Dis, 69:1866-1872 (2009).
Hysi, et al., Human Molecular Genetics, 14(7):935-941 (2005).
Ikeda, et al., Arthritis Research & Therapy, 16:R89 (2014).
Jamontt, et al., Journal of Immunology, 190:2948-2958 (2013).
Jun, et al., Journal of Leukocyte Biology, 94:927-932 (2013).
Kruger, et al., European Society for Organ Transplantation, 20:600-607 (2007).
Kvarnhammar, et al., Plos One, 8(7):e68701 (2013).
Liu, et al., Journal of Biological Sciences, 11(5):525-535 (2015).
McGovern, et al., Human Molecular Genetics, 14(10):1245-1250 (2005).
Murias, et al., Pediatric Rheumatology, 12(Suppl. 1):p. 293 (2014).
Nachbur, et al., Nature Communications, 6:6442 (2015).
Natarajan, et al., Journal of Neuroimmunology, 265:51-60 (2013).
Oh, et al., Plos Pathogens, 9(5):e1003351 (2013).
Ospelt, et al., Arthritis & Rheumatism, 60(2):355-363 (2009).
Paim-Marque, et al., Pediatric Rheumatology, 12(Suppl. 1):p. 272 (2014).
Penack, et al., The Journal of Experimental Medicine, 206(10):2101-2110 (2009).
Peng, et al., International Immunopharmacology, 13:440-445 (2012).

(56) References Cited

OTHER PUBLICATIONS

Pillai, et al., *Seminars in Ophthalmology*, 28(5-6):327-332 (2013).
Plantinga, et al., *Rheumatology*, 52:806-814 (2013).
Rebane, et al., *The Journal of Allergy & Clinical Immunology*, 129:1297-1306 (2012).
Rosenzweig, et al., *Arthritis & Rheumatism*, 62(4):1051-1059 (2010).
Rosenzweig, et al., *Inflammation Research*, 60:705-714 2011).
Rosenzweig, et al., *Investigative Ophthalmology & Visual Science*, 50(4):1746-1753 (2009).
Rosenzweig, et al., *Investigative Ophthalmology & Visual Science*, 50(4):1739-1745 (2009).
Saha, et al., *Cell Host & Microbe*, 5:137-150 (2009).
Sfriso, et al., *Autoimmunity Reviews*, 12:44-51 (2012).
Shaw, et al., *Immunity*, 34:75-84 (2011).
Shigeoka, et al., *The Journal of Immunology*, 184:2297-2304 (2010).
Uehara, et al., *Diagnostic Pathology*, 4(23):1746 (2009).
Vieira, et al., *The Journal of Immunology*, 188:5116-5122 (2012).
Walsh, et al., *Cytokine & Growth Factor Reviews*, 24:91-104 (2013).
Wiken, et al., *The Journal of Clinical Immunology*, 29:78-89 (2009).
Yu, et al., *Plos One*, 6(8):e23855 (2011).
Zhou, et al., *Diabetes & Metabolism*, 38:538-543 (2012).

QUINAZOLINES AS KINASE INHIBITORS

This application is a §371 of International Application No. PCT/IB2014/059094, filed 19 Feb. 2014, which claims priority of U.S. Provisional Application No. 61/767,423, filed 21 Feb. 2013.

FIELD OF THE INVENTION

The present invention relates to quinazolines that inhibit RIP2 kinase and methods of making and using the same.

BACKGROUND OF THE INVENTION

Receptor interacting protein-2 (RIP2) kinase, which is also referred to as CARD3, RICK, CARDIAK, or RIPK2, is a TKL family serine/threonine protein kinase involved in innate immune signaling. RIP2 kinase is composed of an N-terminal kinase domain and a C-terminal caspase-recruitment domain (CARD) linked via an intermediate (IM) region ((1998) *J. Biol. Chem.* 273, 12296-12300; (1998) *Current Biology* 8, 885-889; and (1998) *J. Biol. Chem.* 273, 16968-16975). The CARD domain of RIP2 kinase mediates interaction with other CARD-containing proteins, such as NOD1 and NOD2 ((2000) *J. Biol. Chem.* 275, 27823-27831 and (2001) *EMBO reports* 2, 736-742). NOD1 and NOD2 are cytoplasmic receptors which play a key role in innate immune surveillance. They recognize both gram positive and gram negative bacterial pathogens and are activated by specific peptidoglycan motifs, diaminopimelic acid (i.e., DAP) and muramyl dipeptide (MDP), respectively ((2007) *J Immunol* 178, 2380-2386).

Following activation, RIP2 kinase associates with NOD1 or NOD2 and appears to function principally as a molecular scaffold to bring together other kinases (TAK1, IKKα/β/γ) involved in NF-κB and mitogen-activated protein kinase activation ((2006) *Nature Reviews Immunology* 6, 9-20). RIP2 kinase undergoes a K63-linked polyubiquitination on lysine-209 which facilitates TAK1 recruitment ((2008) *EMBO Journal* 27, 373-383). This post-translational modification is required for signaling as mutation of this residue prevents NOD1/2 mediated NF-kB activation. RIP2 kinase also undergoes autophosphorylation on serine-176, and possibly other residues ((2006) *Cellular Signalling* 18, 2223-2229). Studies using kinase dead mutants (K47A) and non-selective small molecule inhibitors have demonstrated that RIP2 kinase activity is important for regulating the stability of RIP2 kinase expression and signaling ((2007) *Biochem J* 404, 179-190 and (2009) *J. Biol. Chem.* 284, 19183-19188).

Dysregulation of RIP2-dependent signaling has been linked to autoinflammatory diseases. Gain-of-function mutations in the NACHT-domain of NOD2 cause Blau Syndrome, early-onset sarcoidosis, a pediatric granulomateous disease characterized by uveitis, dermatitis, and arthritis ((2001) *Nature Genetics* 29, 19-20; (2005) *Journal of Rheumatology* 32, 373-375; (2005) *Current Rheumatology Reports* 7, 427-433; (2005) *Blood* 105, 1195-1197; (2005) European *Journal of Human Genetics* 13, 742-747; (2006) *American Journal of Ophthalmology* 142, 1089-1092; (2006) *Arthritis & Rheumatism* 54, 3337-3344; (2009) *Arthritis & Rheumatism* 60, 1797-1803; and (2010) *Rheumatology* 49, 194-196). Mutations in the LRR-domain of NOD2 have been strongly linked to susceptibility to Crohn's Disease ((2002) *Am. J. Hum. Genet.* 70, 845-857; (2004) *European Journal of Human Genetics* 12, 206-212; (2008) *Mucosal Immunology* (2008) 1 (Suppl 1), S5-S9. 1, S5-S9; (2008) *Inflammatory Bowel Diseases* 14, 295-302; (2008) *Experimental Dermatology* 17, 1057-1058; (2008) *British Medical Bulletin* 87, 17-30; (2009) *Inflammatory Bowel Diseases* 15, 1145-1154 and (2009) *Microbes and Infection* 11, 912-918). Mutations in NOD1 have been associated with asthma ((2005) *Hum. Mol. Genet.* 14, 935-941) and early-onset and extraintestinal inflammatory bowel disease ((2005) *Hum. Mol. Genet.* 14, 1245-1250). Genetic and functional studies have also suggested a role for RIP2-dependent signaling in a variety of other granulomateous disorders, such as sarcoidosis ((2009) *Journal of Clinical Immunology* 29, 78-89 and (2006) *Sarcoidosis Vasculitis and Diffuse Lung Diseases* 23, 23-29) and Wegner's Granulomatosis ((2009) *Diagnostic Pathology* 4, 23).

A potent, selective, small molecule inhibitor of RIP2 kinase activity would block RIP2-dependent pro-inflammatory signaling and thereby provide a therapeutic benefit in autoinflammatory and/or autoimmune diseases characterized by increased and/or dysregulated RIP2 kinase activity.

SUMMARY OF THE INVENTION

The invention is directed to a compound selected from:

6-(tert-butylsulfonyl)-N-(4,5-dimethyl-1H-pyrazol-3-yl)-7-(2-methoxyethoxy)quinazolin-4-amine, having the formula:

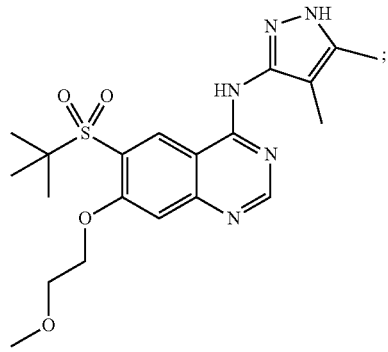 [SMILES: COCCOc1cc2ncnc(Nc3n[nH]c(C)c3C)c2cc1S(=O)(=O)C(C)(C)C]

6-(tert-butylsulfonyl)-N-(4,5-dimethyl-1H-pyrazol-3-yl)-7-ethoxyquinazolin-4-amine having the formula:

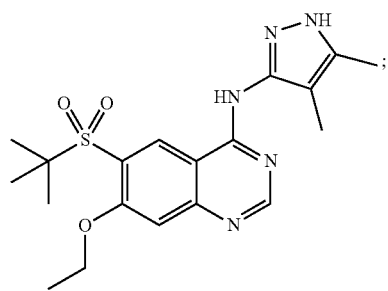 [SMILES: CCOc1cc2ncnc(Nc3n[nH]c(C)c3C)c2cc1S(=O)(=O)C(C)(C)C]

6-(tert-butylsulfonyl)-N-(4,5-dimethyl-1H-pyrazol-3-yl)-7-propoxyquinazolin-4-amine, having the formula:

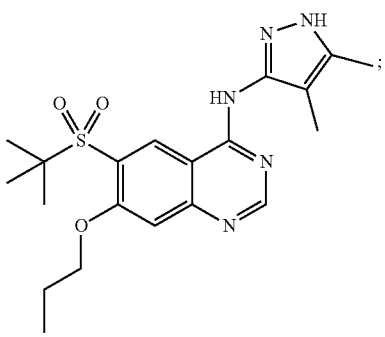 [SMILES: CCCOc1cc2ncnc(Nc3n[nH]c(C)c3C)c2cc1S(=O)(=O)C(C)(C)C]

and 6-(tert-butylsulfonyl)-N-(4,5-dimethyl-1H-pyrazol-3-yl)-7-((tetrahydrofuran-2-yl)methoxy)quinazolin-4-amine, having the formula:

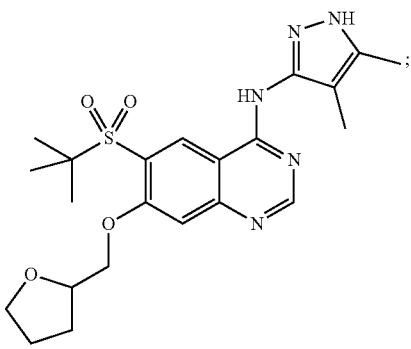 [SMILES: Cc1[nH]nc(Nc2ncnc3cc(OCC4CCCO4)c(S(=O)(=O)C(C)(C)C)cc23)c1C]

or a salt, particularly a pharmaceutically acceptable salt, thereof.

Accordingly, the present invention is directed to a method of inhibiting RIP2 kinase which method comprises contacting a cell with a compound of the invention, or a salt, particularly a pharmaceutically acceptable salt, thereof.

The invention is further directed to a method of treating a RIP2 kinase-mediated disease or disorder which comprises administering a therapeutically effective amount of a compound of the invention, or a salt, particularly a pharmaceutically acceptable salt thereof, to a patient (a human or other mammal, particularly, a human) in need thereof. The invention is still further directed to the use of a compound of the invention or a pharmaceutical composition comprising a compound of the invention to inhibit RIP2 kinase and/or treat a RIP2 kinase-mediated disease or disorder.

Examples of RIP2 kinase-mediated diseases or disorders include uveitis, Crohn's disease, ulcerative colitis, early-onset and extraintestinal inflammatory bowel disease and granulomateous disorders, such as sarcoidosis, Blau syndrome, early-onset sarcoidosis and Wegner's Granulomatosis.

The present invention is further directed to a pharmaceutical composition comprising a compound of the invention, or a salt, particularly a pharmaceutically acceptable salt, thereof and a pharmaceutically acceptable excipient. Particularly, this invention is directed to a pharmaceutical composition for the treatment of a RIP2 kinase-mediated disease or disorder, where the composition comprises a compound of the invention, or a salt, particularly a pharmaceutically acceptable salt, thereof and one or more pharmaceutically acceptable excipients.

DETAILED DESCRIPTION OF THE INVENTION

Figure 1:
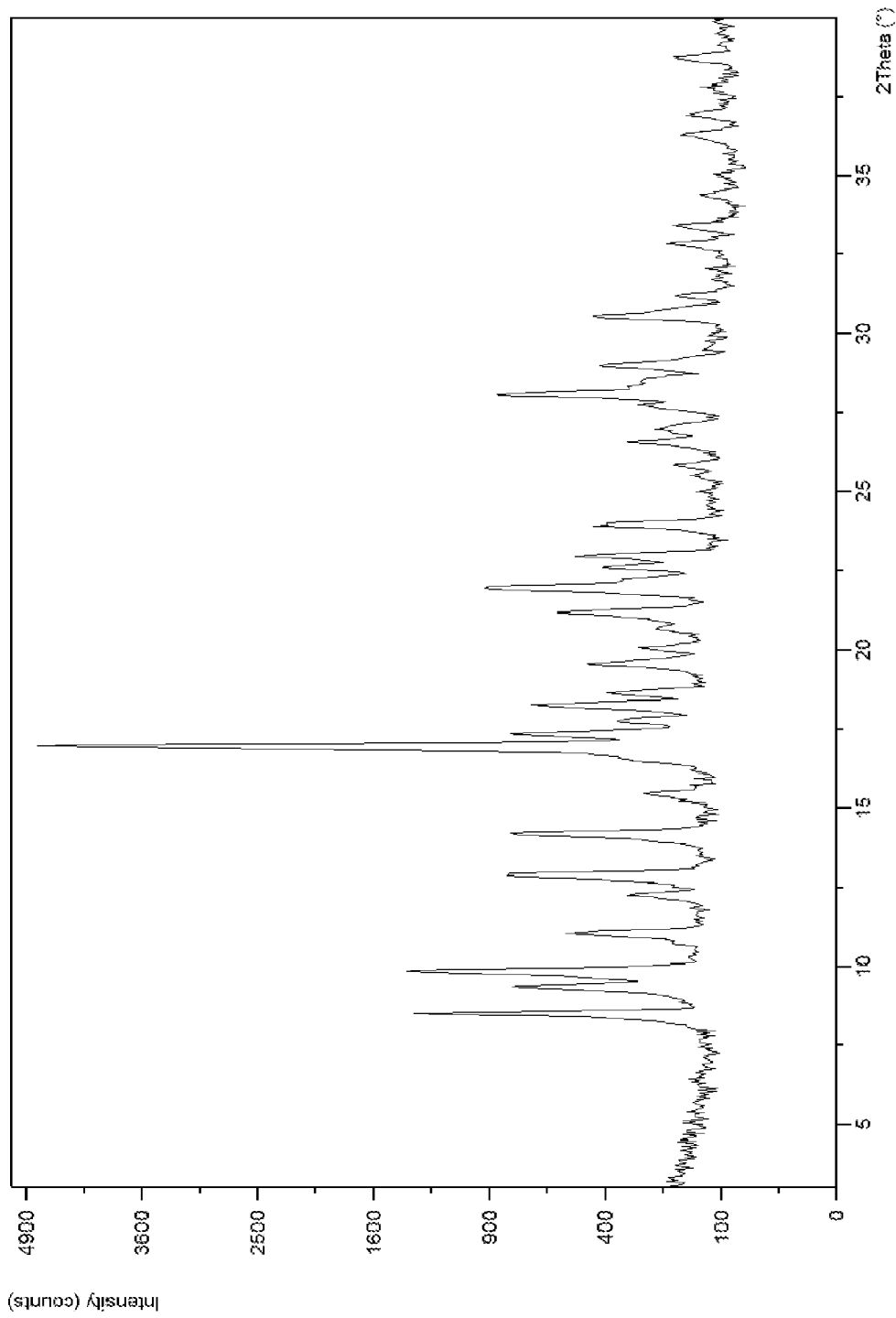
FIG. 1 is a powder x-ray powder diffraction (PXRD) pattern of a crystalline form of 6-(tert-butylsulfonyl)-N-(4,5-dimethyl-1H-pyrazol-3-yl)-7-ethoxyquinazolin-4-amine (free base).

As used herein, the terms "compound(s) of the invention" or "compound(s) of this invention" mean any of the compounds defined herein, in any form, i.e., any salt or non-salt form (e.g., as a free acid or base form, or as a salt, particularly a pharmaceutically acceptable salt thereof) and any physical form thereof (e.g., including non-solid forms (e.g., liquid or semi-solid forms), and solid forms (e.g., amorphous or crystalline forms, specific polymorphic forms, solvate forms, including hydrate forms (e.g., mono-, di- and hemi-hydrates)), and mixtures of various forms (a hydrate of a salt). Specifically, it will be appreciated that the present invention encompasses the compounds of the invention as the free base and as salts thereof, for example as a pharmaceutically acceptable salt thereof. In one embodiment the invention relates to the compounds of the invention in the form of a free base. In another embodiment, the invention relates to the compounds of the invention in the form of a salt, particularly, a pharmaceutically acceptable salt.

It will also be appreciated by those skilled in the art that the pyrazolyl moiety present in the compounds of this invention may exist as tautomeric pyrazolyl isomers represented by Formula (I-A) and Formula (I-B):

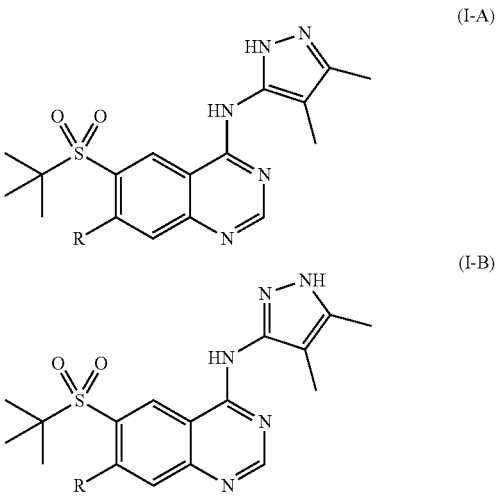

It will be understood that the resulting pyrazolyl moiety may be named as either a 3,4-dimethyl-1H-pyrazol-5-yl moiety or a 4,5-dimethyl-1H-pyrazol-3-yl moiety. It is to be understood that any reference to a named compound of this invention is intended to encompass all tautomers of the named compound and any mixtures of tautomers of the named compound. For example, the compound name 6-(tert-butylsulfonyl)-N-(4,5-dimethyl-1H-pyrazol-3-yl)-7-ethoxyquinazolin-4-amine is intended to encompass compounds 6-(tert-butylsulfonyl)-N-(4,5-dimethyl-1H-pyrazol-3-yl)-7-ethoxyquinazolin-4-amine and 6-(tert-butyl sulfonyl)-N-(3,4-dimethyl-1H-pyrazol-5-yl)-7-ethoxyquinazolin-4-amine, and mixtures thereof. All tautomeric forms of the compounds described herein are intended to be encompassed within the scope of the present invention.

The compounds of the invention may contain one or more asymmetric centers (also referred to as a chiral center) and may, therefore, exist as individual enantiomers, diastereomers, or other stereoisomeric forms, or as mixtures thereof. Chiral centers, such as a chiral carbon, may also be present in the compounds of this invention. Where the stereochemistry of a chiral center present in a compound of this invention (e.g., compound name) or in any chemical structure illustrated herein is not specified, the compound, compound name, or structure is intended to encompass all individual stereoisomers and all mixtures thereof. Thus, compounds of the invention containing one or more chiral center may be present as racemic mixtures, enantiomerically enriched mixtures, or as enantiomerically pure individual stereoisomers.

Individual stereoisomers of a compound of the invention which contain one or more asymmetric center may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

It is to be understood that a solid form of a compound of the invention may exist in crystalline forms, non-crystalline forms or a mixture thereof. Such crystalline forms may also exhibit polymorphism (i.e. the capacity to occur in different crystalline forms). These different crystalline forms are typically known as "polymorphs." Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. One of ordinary skill in the art will appreciate that different polymorphs may be produced, for example, by changing or adjusting the conditions used in crystallizing/recrystallizing the compound.

It is well known and understood to those skilled in the art that the apparatus employed, humidity, temperature, orientation of the powder crystals, and other parameters involved in obtaining a powder X-ray diffraction (PXRD) pattern may cause some variability in the appearance, intensities, and positions of the lines in the diffraction pattern. A powder X-ray diffraction pattern that is "substantially in accordance" with that of the Figure provided herein is a PXRD pattern that would be considered by one skilled in the art to represent a compound possessing the same crystal form as the compound that provided the PXRD pattern of the Figure. For example, the PXRD pattern may be identical to that of FIG. 1, or more likely it may be somewhat different. Such a PXRD pattern may not necessarily show each of the lines of the diffraction patterns presented herein, and/or may show a slight change in appearance, intensity, or a shift in position of said lines resulting from differences in the conditions involved in obtaining the data. A person skilled in the art is capable of determining if a sample of a crystalline compound has the same form as, or a different form from, a form disclosed herein by comparison of their PXRD patterns. For example, one skilled in the art can overlay a PXRD pattern of a sample of a crystalline form of 2,6-(tert-butylsulfonyl)-N-(4,5-dimethyl-1H-pyrazol-3-yl)-7-ethoxyquinazolin-4-amine (free base) with the PXRD pattern of FIG. 1, and using expertise and knowledge in the art, readily determine whether the PXRD pattern of the sample is substantially in accordance with the PXRD pattern of FIG. 1. If the PXRD pattern is substantially in accordance with FIG. 1, the sample form can be readily and accurately identified as having the same form as the crystalline form of 6-(tert-butylsulfonyl)-N-(4,5-dimethyl-1H-pyrazol-3-yl)-7-ethoxyquinazolin-4-amine (free base) described herein. Similarly, a person skilled in the art is capable of determining if a given diffraction angle (expressed in ° 2θ) obtained from a PXRD pattern is at about the same position as a recited value.

Because of their potential use in medicine, the salts of the compounds of this invention are preferably pharmaceutically acceptable salts. Suitable pharmaceutically acceptable salts include acid or base addition salts, such as those described by Berge, Bighley and Monkhouse J. Pharm. Sci (1977) 66, pp 1-19 and "Pharmaceutical Salts: Properties, Selection, and Use, 2nd Revised Edition," P. H. Stahl and C. G. Wermuth (eds.), Wiley, Hoboken, N.J., US (2011).

The term "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

"Pharmaceutically acceptable salt(s)" refers to a compound which is suitable for pharmaceutical use. Salt and solvate (e.g. hydrates and hydrates of salts) froms of the compounds of the invention which are suitable for use in medicine are those wherein the counterion or associated solvent is pharmaceutically acceptable. However, salts and solvates having non-pharmaceutically acceptable counterions or associated solvents are within the scope of the present invention, for example, for use as intermediates in the preparation of other compounds of the invention and their salts and solvates.

When a compound of the invention is a base (contains a basic moiety), a desired salt form may be prepared by any suitable method known in the art, including treatment of the free base with an acid. Examples of pharmaceutically acceptable acid-addition salts include acetate, adipate, ascorbate, aspartate, benzenesulfonate, benzoate, camphorate, camphor-sulfonate (camsylate), caprate (decanoate), caproate (hexanoate), caprylate (octanoate), carbonate, bicarbonate, cinnamate, citrate, cyclamate, dodecylsulfate (estolate), ethane-1,2-disulfonate (edisylate), ethanesulfonate (esylate), formate, fumarate, galactarate (mucate), gentisate (2,5-dihydroxybenzoate), glucoheptonate (gluceptate), gluconate, glucuronate, glutamate, glutarate, glycerophosphorate, glycolate, hippurate, hydrobromide, hydrochloride, hydroiodide, isobutyrate, lactate, lactobionate, laurate, maleate, malate, malonate, mandelate, methanesulfonate (mesylate), naphthalene-1,5-disulfonate (napadisylate), naphthalene-sulfonate (napsylate), nicotinate, nitrate, oleate, oxalate, palmitate, pamoate, phosphate, diphosphate, proprionate, pyroglutamate, salicylate, sebacate, stearate, succinate, sulfate, tartrate, thiocyanate, tosylate, undecylenate, 1-hydroxy-2-naphthoate, 2,2-dichloroacetate, 2-hydroxyethanesulfonate (isethionate), 2-oxoglutarate, 4-acetamidobenzoate, and 4-aminosalicylate. Non-pharmaceutically acceptable salts, e.g. trifluoroacetate, may be used, for example in the isolation of a compound of the invention, and are included within the scope of this invention.

When a compound of the invention is an acid (contains an acidic moiety), a desired salt form may be prepared by any suitable method known to the art, including treatment of the free acid with an inorganic or organic base. Examples of pharmaceutically acceptable base-addition salts include ammonium, lithium, sodium, potassium, calcium, magnesium, aluminum salts, zinc salts, trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, glucamine, N-methylglucamine, collidine, quinine, quinoline, lysine and arginine. In one embodiment, the pharmaceutically acceptable base-addition salt is sodium.

Certain of the compounds of the invention may form salts with one or more equivalents of an acid (if the compound contains a basic moiety) or a base (if the compound contains an acidic moiety). The present invention includes within its scope all possible stoichiometric and non-stoichiometric salt forms.

This invention also provides for the conversion of one pharmaceutically acceptable salt of a compound of this invention into another pharmaceutically acceptable salt of a compound of this invention.

If a basic compound is isolated as a salt, the corresponding free acid or free base form of that compound may be prepared by any suitable method known to the art.

For solvates of the compounds of the invention, including solvates of salts of the compounds of the invention, that are in crystalline form, the skilled artisan will appreciate that pharmaceutically acceptable solvates may be formed wherein solvent molecules are incorporated into the crystalline lattice during crystallization. Solvates may involve nonaqueous solvents such as ethanol, isopropanol, DMSO, acetic acid, ethanolamine, and EtOAc, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing variable amounts of water. The invention includes all such solvates, particularly hydrates.

Because the compounds of the invention are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

General Synthetic Methods

The compounds of the invention may be obtained by using synthetic procedures illustrated in the Schemes below or by drawing on the knowledge of a skilled organic chemist.

The syntheses provided in these Schemes are applicable for producing compounds of the invention having a variety of different substituent groups employing appropriate precursors, which are suitably protected if needed, to achieve compatibility with the reactions outlined herein. Subsequent deprotection, where needed, affords compounds of the nature generally disclosed. While the Schemes are shown with compounds only of a generic formula, they are illustrative of processes that may be used to make the compounds of the invention.

Substitution at C6 could be installed prior to installation of the pyrazolyl moiety. A palladium catalyzed coupling of a thiol with the 6-iodoquinazolinone can provide a sulfide which can subsequently be oxidized to the sulfone. Chlorination with $POCl_3$ or $SOCl_2$ may provide the 4-chloroquinazoline.

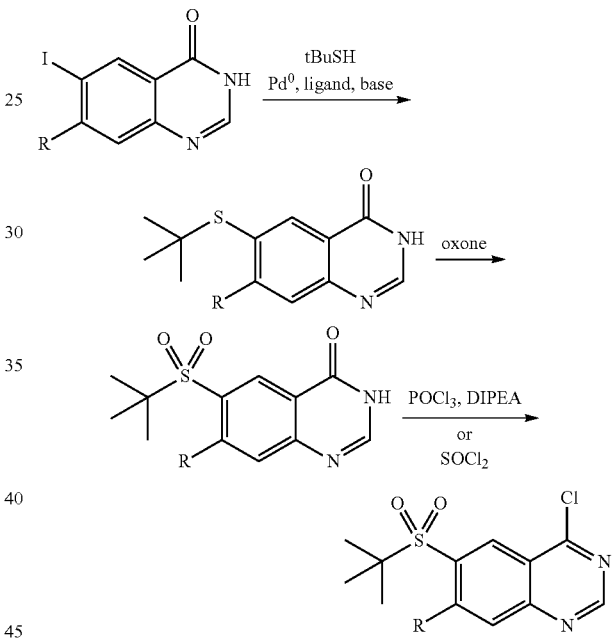

Scheme 1

Anilines/amines could be reacted with 4-chloro-quinazolines under basic or acidic conditions to afford 4-aminoquinazolines which could be final compounds or used as intermediates for further synthesis.

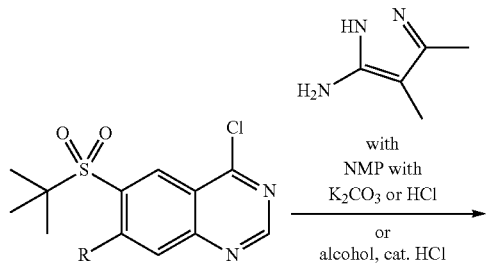

Scheme 2

-continued

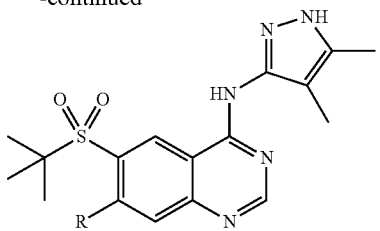

Preparation of some compounds of the invention alternatively may be prepared from 6-bromo-7-fluoroquinazolin-4-ol via reaction with suitable alcohols in the presence of base with heating to give the appropriate 6-bromo-7-alkoxyquinazolin-4-ol. Subsequent chlorination and displacement by amines/anilines will afford 4-amino-6-bromo-7-alkoxyquinzolines. Further reaction of these compounds with thiols or thiolates in the presence of a suitable combination of palladium catalyst, ligand and base with heating will provide 4-amino-6-alkylthio-7-alkoxyquinazolines. Oxidation will result in 4-amino-6-sulfonyl-7alkoxyquinazolines which can be final compounds or utilized as intermediates in further chemistry.

Scheme 3

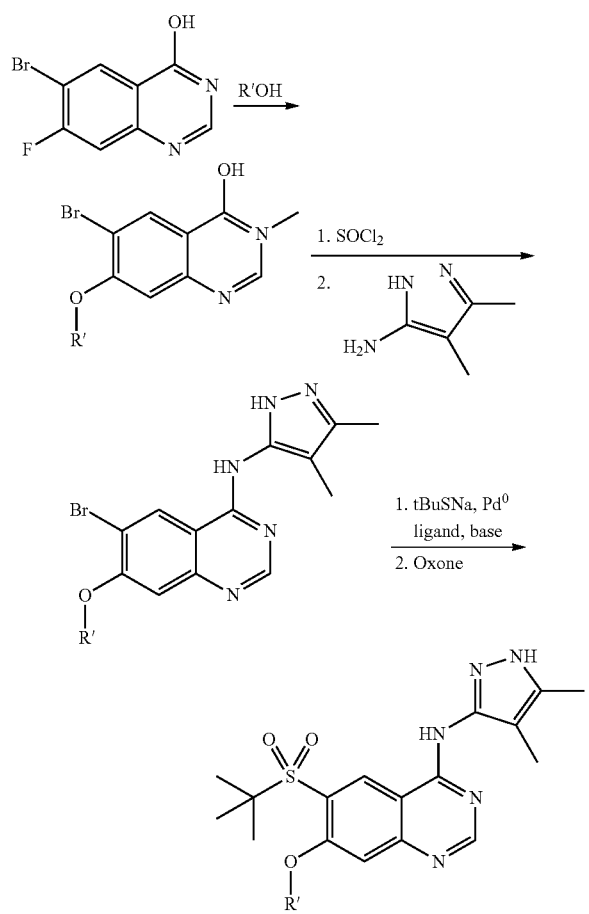

Preparation of some of the compounds of the invention can be accomplished from the 7-fluoro-6-sulfonyl-4-quinazolinone. Synthesis of this intermediate begins with bromination of 4-fluoro-2-aminobenzoic acid followed by a condensation with formamidine acetate in situ. A palladium catalyzed coupling with a thiol provides the sulfide which is subsequently oxidized to the sulfone.

Scheme 4

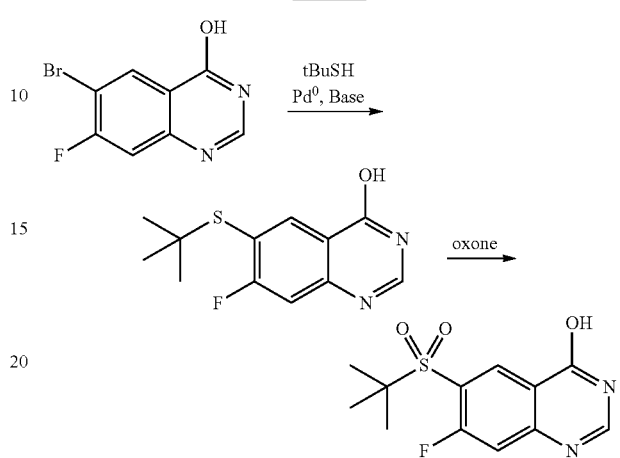

Substitution of the fluoro substituent for an alkoxy group can be achieved by treatment with the appropriate alcohol and potassium t-butoxide.

Scheme 5

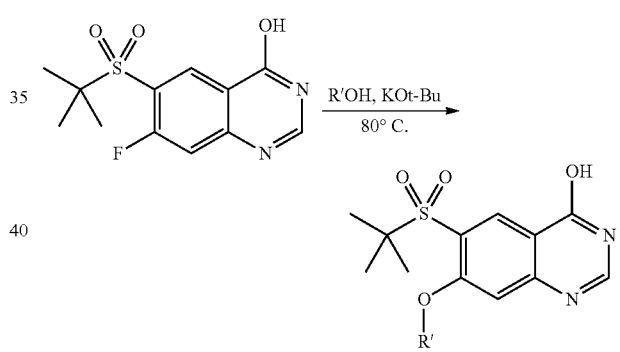

A particular compound of the invention is 6-(tert-butylsulfonyl)-N-(4,5-dimethyl-1H-pyrazol-3-yl)-7-ethoxyquinazolin-4-amine (as the free base). In another embodiment, a particular compound of the invention is 6-(tert-butylsulfonyl)-N-(4,5-dimethyl-1H-pyrazol-3-yl)-7-ethoxyquinazolin-4-amine or a salt thereof. In another embodiment, a particular compound of the invention is 6-(tert-butylsulfonyl)-N-(4,5-dimethyl-1H-pyrazol-3-yl)-7-ethoxyquinazolin-4-amine or a pharmaceutically acceptable salt thereof. In another embodiment, a particular compound of the invention is a crystalline form of 6-(tert-butylsulfonyl)-N-(4,5-dimethyl-1H-pyrazol-3-yl)-7-ethoxyquinazolin-4-amine characterized by the PXRD pattern of FIG. 1. In yet another embodiment, a particular compound of the invention is a crystalline form of 6-(tert-butylsulfonyl)-N-(4,5-dimethyl-1H-pyrazol-3-yl)-7-ethoxyquinazolin-4-amine characterized by the diffraction data in Table 1.

The compounds of this invention are inhibitors of RIP2 kinase. Accordingly, in one embodiment, the invention is directed to a method of inhibiting RIP2 kinase comprising contacting a cell with a compound of the invention. In another embodiment, the invention is directed to a method of treating a RIP2 kinase-mediated disease or disorder comprising administering a therapeutically effective amount of a compound of the invention to a human in need thereof.

In another particular embodiment, the invention is directed to a method of treating a RIP2 kinase-mediated disease or disorder comprising administering a therapeutically effective amount of 6-(tert-butylsulfonyl)-N-(4,5-dimethyl-1H-pyrazol-3-yl)-7-ethoxyquinazolin-4-amine, or a pharmaceutically acceptable salt thereof, to a human in need thereof.

The compounds of the invention may be particularly useful for treatment of RIP2 kinase-mediated diseases or disorders, particularly diseases or disorders where inhibition of RIP2 kinase would provide benefit. Examples of such RIP2 kinase mediated diseases or disorders include uveitis, interleukin-1 converting enzyme (ICE, also known as Caspase-1) associated fever syndrome (ICE fever), dermatitis, acute lung injury, type 2 diabetes mellitus, arthritis (specifically rheumatoid arthritis), inflammatory bowel disorders (such as ulcerative colitis and Crohn's disease), early-onset inflammatory bowel disease, extra-intestinal inflammatory bowel disease, prevention of ischemia reperfusion injury in solid organs (specifically kidney) in response ischemia induced by cardiac surgery, organ transplant, sepsis and other insults, liver diseases (non-alcohol steatohepatitis, alcohol steatohepatitis, and autoimmune hepatitis), allergic diseases (such as asthma), transplant reactions (such as graft versus host disease), autoimmune diseases (such as systemic lupus erythematosus, and multiple sclerosis), and granulomateous disorders (such as sarcoidosis, Blau syndrome, early-onset sarcoidosis, Wegner's granulomatosis, and interstitial pulmonary disease).

The compounds of this invention may be particularly useful in the treatment of uveitis, ICE fever, Blau Syndrome, early-onset sarcoidosis, ulcerative colitis, Crohn's disease, Wegener's granulamatosis and sarcoidosis. Treatment of RIP2 kinase-mediated diseases or disorders, or more broadly, treatment of immune mediated diseases including, but not limited to, allergic diseases, autoimmune diseases, prevention of transplant rejection and the like, may be achieved using a compound of this invention as a monotherapy, or in dual or multiple combination therapy, particularly for the treatment of refractory cases, such as in combination with other anti-inflammatory and/or anti-TNF agents, which may be administered in therapeutically effective amounts as is known in the art.

The compounds of this invention may be employed alone or in combination with other therapeutic agents. Combination therapies according to the present invention thus comprise the administration of at least one compound of the invention, and the use of at least one other therapeutically active agent. Preferably, combination therapies according to the present invention comprise the administration of at least one compound of the invention, and at least one other therapeutically active agent. The compound(s) of the invention and the other therapeutically active agent(s) may be administered together in a single pharmaceutical composition or separately and, when administered separately this may occur simultaneously or sequentially in any order. The amounts of the compound(s) of the invention and the other therapeutically active agent(s) and the relative timings of administration will be selected in order to achieve the desired combined therapeutic effect. Thus in a further aspect, there is provided a combination comprising a compound of the invention together with one or more other therapeutically active agents. In a further aspect, there is provided a combination comprising 6-(tert-butylsulfonyl)-N-(4,5-dimethyl-1H-pyrazol-3-yl)-7-ethoxyquinazolin-4-amine, or a pharmaceutically acceptable salt thereof, together with one or more other therapeutically active agents.

Thus in one aspect of this invention, a compound of the invention and pharmaceutical compositions comprising a compound of the invention may be used in combination with or include one or more other therapeutic agents, for example an anti-inflammatory agent and/or an anti-TNF agent.

The compounds of this invention may be administered in combination with corticosteroids and/or anti-TNF agents to treat Blau syndrome, early-onset sarcoidosis; or in combination with anti-TNF biologics or other anti-inflammatory biologics to treat Crohn's Disease; or in combination with 5-ASA (mesalamine) or sulfasalazine to treat ulcerative colitis; or in combination with low-dose corticosteroids and/or methotrexate to treat Wegener's granulamatosis or sarcoidosis or interstitial pulmonary disease; or in combination with a biologic (e.g. anti-TNF, anti-IL-6, etc.) to treat rheumatoid arthritis; or in combination with anti-IL6 and/or methotrexate to treat ICE fever.

Examples of suitable anti-inflammatory agents include 5-aminosalicyclic acid and mesalamine preparations, sulfasalazine, hydroxycloroquine, thiopurines (azathioprin, mercaptopurin), methotrexate, cyclophosphamide, cyclosporine, JAK inhibitors (tofacitinib), corticosteroids, particularly low-dose corticosteroids (such as prednisone (Deltasone®) and bundesonide) and anti-inflammatory biologics such as anti-IL6R mAbs (Actemra® (tocilizumab)), anti-IL6 biologics, anti-IL1 or IL12 or IL23 biologics (ustekinumab (Stelara®)), anti-integrin agents (natalizumab (Tysabri®)), anti-CD20 mAbs (rituximab (Rituxan®) and ofatumumab (Arzerra®)), and other agents, such as abatacept (Orencia®), anakinra (Kineret®), and belimumab (Benlysta®), CD4 biologics and other cytokine inhibitors or biologics to T-cell or B-cell receptors or interleukins. Examples of suitable anti-TNF agents include the anti-TNF biologics such as Enbrel® (etanecerpt), Humira® (adalimumab), Remicade® (infliximab), Cimzia® (certolizumab), and Simponi® (golimumab).

Other examples of suitable anti-inflammatory agents include 5-aminosalicyclic acid and mesalamine preparations, sulfasalazine, hydroxycloroquine, thiopurines (azathioprin, mercaptopurin), methotrexate, cyclophosphamide, cyclosporine, calcineurin inhibitors (cyclosporine, pimecrolimus, tacrolimus), mycophenolic acid (CellCept®), mTOR inhibitors (temsirolimus, everolimus), JAK inhibitors (tofacitinib), (Xeljan®)), Syk inhibitors (fostamatinib), corticosteroids, particularly low-dose corticosteroids (such as prednisone (Deltasone®) and bundesonide) and anti-inflammatory biologics such as anti-IL6R mAbs (Actemra® (tocilizumab)), anti-IL6 biologics, anti-IL1 (anakinra (Kineret®), canakinumab (Ilaris®), rilonacept (Arcalyst®)), anti- or IL12 or and IL23 biologics (ustekinumab (Stelara®)), anti-IL17 biologics (secukinumab), anti-CD22 (epratuzumab), anti-integrin agents (natalizumab (Tysabri®)), vedolizumab (Entyvio®)), anti-IFNa (sifalimumab), anti-CD20 mAbs (rituximab (Rituxan®) and ofatumumab (Arzerra®)), and other agents, such as abatacept (Orencia®), anakinra (Kineret®), canakinumab (Ilaris®), rilonacept (Arcalyst®), secukinumab, epratuzumab, sifalimumab, and belimumab (Benlysta®), CD4 biologics and other cytokine inhibitors or biologics to T-cell or B-cell receptors or interleukins. Examples of suitable anti-TNF agents include the anti-TNF biologics such as Enbrel® (etanecerpt), Humira® (adalimumab), Remicade® (infliximab), Cimzia® (certolizumab), and Simponi® (golimumab). This invention also provides a compound of the invention for use in therapy. Specifically, this invention provides the compounds described herein, or a pharmaceutically acceptable salt thereof, for use in therapy. More specifically, this invention provides 6-(tert-butylsulfonyl)-N-(4,5-dimethyl-1H-pyrazol-3-yl)-7-ethoxyquinazolin-4-amine, or a pharmaceutically acceptable salt thereof, for use in therapy.

In another embodiment, this invention provides a compound of the invention for use in the treatment of a RIP2 kinase mediated disease or disorder. Specifically, this invention provides the compounds described herein, or a pharmaceutically acceptable salt thereof, for use in the treatment of a RIP2 kinase mediated disease or disorder.

In another embodiment this invention provides the compounds described herein, or a pharmaceutically acceptable salt thereof, for use in the treatment of uveitis, interleukin-1 converting enzyme associated fever syndrome, dermatitis, acute lung injury, type 2 diabetes mellitus, arthritis (specifically rheumatoid arthritis), inflammatory bowel disorders (such as ulcerative colitis and Crohn's disease), early-onset inflammatory bowel disease, extra-intestinal inflammatory bowel disease, prevention of ischemia reperfusion injury in solid organs (specifically kidney) in response ischemia induced by cardiac surgery, organ transplant, sepsis and other insults, liver diseases (non-alcohol steatohepatitis, alcohol steatohepatitis, and autoimmune hepatitis), allergic diseases (such as asthma), transplant reactions (such as graft versus host disease), autoimmune diseases (such as systemic lupus erythematosus, and multiple sclerosis), and granulomateous disorders (such as sarcoidosis, Blau syndrome, early-onset sarcoidosis, Wegner's granulomatosis, or interstitial pulmonary disease).

In another embodiment this invention provides the compounds described herein, or a pharmaceutically acceptable salt thereof, for use in the treatment of uveitis. In another embodiment this invention provides the compounds described herein, or a pharmaceutically acceptable salt thereof, for use in the treatment of interleukin-1 converting enzyme associated fever syndrome. In another embodiment this invention provides the compounds described herein, or a pharmaceutically acceptable salt thereof, for use in the treatment of Blau syndrome. In another embodiment this invention provides the compounds described herein, or a pharmaceutically acceptable salt thereof, for use in the treatment of early-onset sarcoidosis. In another embodiment this invention provides the compounds described herein, or a pharmaceutically acceptable salt thereof, for use in the treatment of ulcerative colitis. In another embodiment this invention provides the compounds described herein, or a pharmaceutically acceptable salt thereof, for use in the treatment of Crohn's disease. In another embodiment this invention provides the compounds described herein, or a pharmaceutically acceptable salt thereof, for use in the treatment of early-onset inflammatory bowel disease. In another embodiment this invention provides the compounds described herein, or a pharmaceutically acceptable salt thereof, for use in the treatment of extraintestinal inflammatory bowel disease. In another embodiment this invention provides the compounds described herein, or a pharmaceutically acceptable salt thereof, for use in the treatment of Wegner's Granulomatosis. In another embodiment this invention provides the compounds described herein, or a pharmaceutically acceptable salt thereof, for use in the treatment of sarcoidosis.

The invention also provides for the use of a compound of the invention in the manufacture of a medicament for use in the treatment of a RIP2 kinase-mediated disease or disorder, for example each of the diseases and disorders recited herein. Specifically, this invention provides for the use of the compounds described herein, or a pharmaceutically acceptable salt thereof, in the manufacture of a medicament for the treatment of a RIP2 kinase mediated disease or disorder. More specifically, this invention provides for the use of 6-(tert-butylsulfonyl)-N-(4,5-dimethyl-1H-pyrazol-3-yl)-7-ethoxyquinazolin-4-amine, or a pharmaceutically acceptable salt thereof, in the manufacture of a medicament for the treatment of a RIP2 kinase mediated disease or disorder.

Accordingly, the invention provides for the use of the compounds described herein, or a pharmaceutically acceptable salt thereof, in the manufacture of a medicament for use in the treatment of a human in need thereof having a disease or disorder mediated by RIP2 kinase. A therapeutically "effective amount" is intended to mean that amount of a compound that, when administered to a patient in need of such treatment, is sufficient to effect treatment, as defined herein. Thus, e.g., a therapeutically effective amount of a compound of the invention, or a pharmaceutically acceptable salt thereof, is a quantity of an inventive agent that, when administered to a human in need thereof, is sufficient to modulate or inhibit the activity of RIP2 kinase such that a disease condition which is mediated by that activity is reduced, alleviated or prevented. The amount of a given compound that will correspond to such an amount will vary depending upon factors such as the particular compound (e.g., the potency ($pIC_{50}$), efficacy ($EC_{50}$), and the biological half-life of the particular compound), disease condition and its severity, the identity (e.g., age, size and weight) of the patient in need of treatment, but can nevertheless be routinely determined by one skilled in the art. Likewise, the duration of treatment and the time period of administration (time period between dosages and the timing of the dosages, e.g., before/with/after meals) of the compound will vary according to the identity of the mammal in need of treatment (e.g., weight), the particular compound and its properties (e.g., pharmaceutical characteristics), disease or disorder and its severity and the specific composition and method being used, but can nevertheless be determined by one of skill in the art.

"Treating" or "treatment" is intended to mean at least the mitigation of a disease or disorder in a patient. The methods of treatment for mitigation of a disease or disorder include the use of the compounds in this invention in any conventionally acceptable manner, for example for prevention, retardation, prophylaxis, therapy or cure of a mediated disease or disorder. Specific diseases and disorders that may be particularly susceptible to treatment using a compound of this invention are described herein.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the disease or disorder being treated, the severity of the disease or disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

For use in therapy, the compounds of the invention will be normally, but not necessarily, formulated into a pharmaceutical composition prior to administration to a patient. Accordingly, the invention also is directed to pharmaceutical compositions comprising a compound of the invention and one or more pharmaceutically acceptable excipients.

In one embodiment, there is provided a pharmaceutical composition comprising 6-(tert-butylsulfonyl)-N-(4,5-dimethyl-1H-pyrazol-3-yl)-7-ethoxyquinazolin-4-amine, or a pharmaceutically acceptable salt thereof, and one or more pharmaceutically acceptable excipients. In another embodiment, there is provided a pharmaceutical composition comprising 6-(tert-butylsulfonyl)-N-(4,5-dimethyl-1H-pyrazol-3-yl)-7-ethoxyquinazolin-4-amine (as the free base) and one or more pharmaceutically acceptable excipients. In another embodiment, there is provided a pharmaceutical composition comprising a crystalline form of 6-(tert-butylsulfonyl)-N-(4,5-dimethyl-1H-pyrazol-3-yl)-7-ethoxyquinazolin-4-amine characterized by the PXRD pattern of FIG. 1 and one or more pharmaceutically acceptable excipients. The pharmaceutical compositions of the invention may be prepared and packaged in bulk form wherein an effective amount of a compound of the invention can be extracted and then given to the patient such as with powders, syrups, and solutions for injection. Alternatively, the pharmaceutical compositions of the invention may be prepared and packaged in unit dosage form. For oral application, for example, one or more tablets or capsules may be administered. A dose of the pharmaceutical composition contains at least a therapeutically effective amount of a compound of this invention. When prepared in unit dosage form, the pharmaceutical compositions may contain from 1 mg to 1000 mg of a compound of this invention.

As provided herein, unit dosage forms (pharmaceutical compositions) containing from 1 mg to 1000 mg of a compound of the invention may be administered one, two, three, or four times per day, preferably one, two, or three times per day, and more preferably, one or two times per day, to effect treatment of a RIP2 mediated disease or disorder.

The pharmaceutical compositions of the invention typically contain one compound of the invention. However, in certain embodiments, the pharmaceutical compositions of the invention contain more than one compound of the invention. In addition, the pharmaceutical compositions of the invention may optionally further comprise one or more additional pharmaceutically active compounds.

As used herein, "pharmaceutically acceptable excipient" means a material, composition or vehicle involved in giving form or consistency to the composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically acceptable.

The compounds of the invention and the pharmaceutically acceptable excipient or excipients will typically be formulated into a dosage form adapted for administration to the patient by the desired route of administration. Conventional dosage forms include those adapted for (1) oral administration such as tablets, capsules, caplets, pills, troches, powders, syrups, elixirs, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols and solutions; and (6) topical administration such as creams, ointments, lotions, solutions, pastes, sprays, foams, and gels.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting the compound or compounds of the invention once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anti-caking agents, humectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising an effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

The invention also includes various deuterated forms of the compounds of the invention. Each available hydrogen atom attached to a carbon atom may be independently replaced with a deuterium atom. A person of ordinary skill in the art will know how to synthesize deuterated forms of the compounds of the invention.

Names for the intermediate and final compounds described herein were generated using the software naming program ACD/Name Pro V6.02 available from Advanced Chemistry Development, Inc., 110 Yonge Street, 14th Floor, Toronto, Ontario, Canada, M5C 1T4 (http://www.acdlabs.com/) or the naming program in ChemDraw, Struct=Name Pro 12.0, as part of ChemBioDraw Ultra, available from CambridgeSoft. 100 CambridgePark Drive, Cambridge, Mass. 02140 USA (www.cambridgesoft.com).

In the following experimental descriptions, the following abbreviations may be used:

| Abbreviation | Meaning |
|---|---|
| brine | saturated aqueous sodium chloride |
| CH$_2$Cl$_2$ or DCM | methylene chloride |
| CH$_3$CN or MeCN or ACN | acetonitrile |
| d | day |
| DMF | N,N-dimethylformamide |
| DIEA | N,N-diisopropylethylamine, Hunig's base |
| DMSO | dimethylsulfoxide |
| equiv | equivalents |
| Et | ethyl |
| Et$_3$N or TEA | triethylamine |
| Et$_2$O | diethyl ether |
| EtOAc | ethyl acetate |
| EtOH | ethanol |
| h, hr | hour(s) |
| HCl | hydrochloric acid |
| KOt-Bu | potassium tert-butoxide |
| LCMS | liquid chromatography-mass spectroscopy |
| Me | methyl |
| MeOH or CH$_3$OH | methanol |
| MgSO$_4$ | magnesium sulfate |
| min | minute(s) |
| MS | mass spectrum |
| nw | microwave |
| Na$_2$SO$_4$ | sodium sulfate |
| NH$_4$OH | ammonium hydroxide |
| POCl$_3$ | phosphoryl chloride |
| Rt, RT | room temperature |
| satd. | saturated |
| 2-MeTHF | 2-methyl-tetrahydrofuran |
| TFA | trifluoroacetic acid |

Preparation 1

6-(tert-Butylsulfonyl)-7-fluoroquinazolin-4-ol

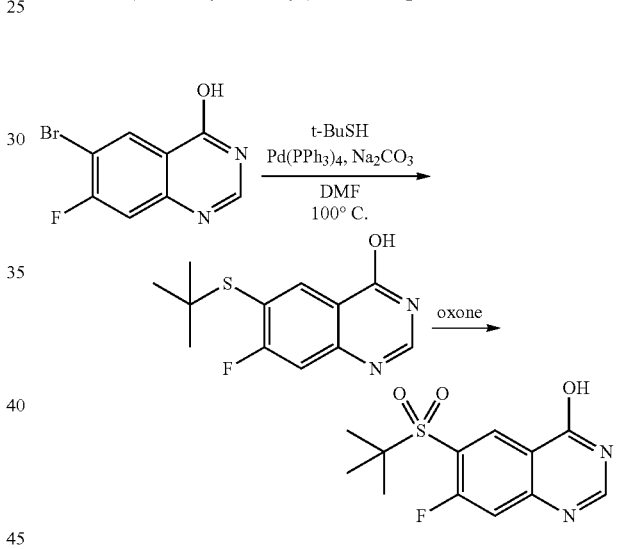

Step 1: 6-(tert-butylthio)-7-fluoroquinazolin-4-ol: A mixture of 6-bromo-7-fluoroquinazolin-4-ol (69 g, 285 mmol), tetrakis(triphenylphosphine)-palladium(0) (20 g, 17 mmol) and sodium carbonate (60 g, 570 mmol) was stirred in DMF (1 L) while purging with nitrogen gas for 5 minutes. 2-Methylpropane-2-thiol (64 ml, 570 mmol) was added and the reaction mixture was heated under reflux condenser for 6 hours at 100° C. The reaction was cooled and filtered thru glass filter paper, and then poured slowly into 1500 mL of stirring water. The resulting red precipitate was filtered and triturated with 200 mL EtOAc. The solid was filtered and washed sequentially with 110 mL hexanes, 150 mL of 90:10 hexanes:EtOAc to give 6-(tert-butylthio)-7-fluoroquinazolin-4-ol (44.5 g, 61.9% yield) as a tan solid. LC/MS: M+H=253.2 $^1$H NMR (400 MHz, DMSO-d$_6$) δ ppm 12.23-12.72 (m, 1H), 8.24 (d, J=8.1 Hz, 1H), 8.19 (s, 1H), 7.58 (d, J=9.6 Hz, 1H), 1.28 (s, 9H).

Step 2: 6-(tert-butylsulfonyl)-7-fluoroquinazolin-4-ol: A suspension of 6-(tert-butylthio)-7-fluoroquinazolin-4-ol (45 g, 124 mmol) and oxone (191 g, 311 mmol) in ethyl acetate (1220 ml), methanol (1220 ml), and water (1220 ml) was stirred for 4 h at 25° C., when another 25 g (2.8 eq total) of oxone was added. The reaction mixture was stirred by overhead stirrer for 12 h. The reaction was filtered, and the filtrate was basified slowly with saturated aqueous sodium bicarbonate, then solid sodium bicarbonate, to pH~7.5. The mixture was extracted with an additional 1.25 L of EtOAc followed by 500 mL EtOAc. The combined organics were washed with brine, then dried over MgSO$_4$, filtered, and concentrated in vacuo. A small impurity was removed by trituration with 200 mL EtOAc. The desired 6-(tert-butyl-sulfonyl)-7-fluoroquinazolin-4-ol (33.2 g, 94% yield) was filtered out as a yellow solid. LC/MS: M+H=285.2 $^1$H NMR (400 MHz, DMSO-d$_6$) δ ppm 12.48-13.03 (m, br. s, 1H), 8.47 (d, J=7.8 Hz, 1H), 8.32 (s, 1H), 7.73 (d, J=11.1 Hz, 1H), 1.17-1.40 (s, 9H).

Preparation 2

6-(tert-butylsulfonyl)-N-(4,5-dimethyl-1H-pyrazol-3-yl)-7-fluoroquinazolin-4-amine

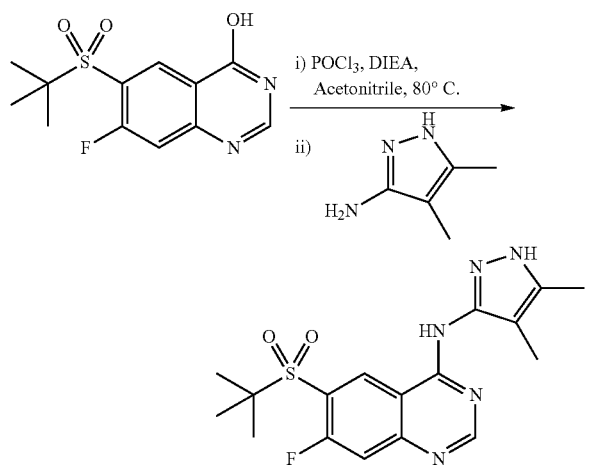

To a solution of 6-(tert-butylsulfonyl)-7-fluoroquinazolin-4-ol (4.14 g, 14.56 mmol) in acetonitrile (42.7 ml) was added POCl$_3$ (2.036 ml, 21.84 mmol) and DIEA (3.81 ml, 21.84 mmol). The reaction was heated at 80° C. overnight for 16 h. Additional POCl$_3$ was added (500 uL) and the reaction stirred at 80° C. for 18 h. Complete conversion to chloride was observed via LCMS. 4,5-Dimethyl-1H-pyrazol-3-amine (1.942 g, 17.47 mmol) was added and the reaction was stirred for 1 h at 80° C. The precipitate was filtered, washed with acetonitrile and dried to afford 6-(tert-butylsulfonyl)-N-(4,5-dimethyl-1H-pyrazol-3-yl)-7-fluoroquinazolin-4-amine, hydrochloride (4.15 g, 9.93 mmol, 68.2% yield). $^1$H NMR (400 MHz, DMSO-d$_6$) δ ppm 9.10-9.44 (m, 1H) 8.88 (br. s., 1H) 7.94 (d, J=10.36 Hz, 1H) 2.23 (s, 3H) 1.82 (s, 3H) 1.24-1.45 (m, 9H). MS (m\z) 378 (M+H)+.

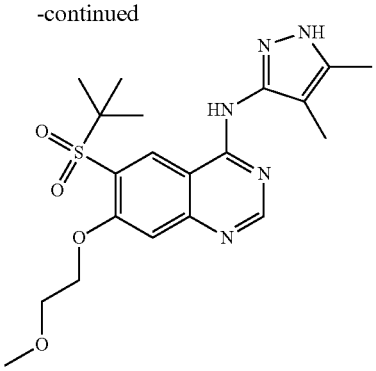

Example 1

6-(tert-Butylsulfonyl)-N-(4,5-dimethyl-1H-pyrazol-3-yl)-7-(2-methoxyethoxy)quinazolin-4-amine A mixture of 6-(tert-butylsulfonyl)-N-(4,5-dimethyl-1H-pyrazol-3-yl)-'7-fluoroquinazolin-4-amine, hydrochloride (300 mg, 0.73 mmol), 2-methoxyethanol (5.7 ml, 73 mmol) and KOtBu (410 mg, 3.6 mmol) was heated at 90° C. for 4 d. The reaction was concentrated to dryness, dry-loaded onto silica gel and purified via column chromatography (ISCO-Rf, 0-25% methanol (w/1% NH$_4$OH)/ethyl acetate to afford 6-(tert-butylsulfonyl)-N-(4,5-dimethyl-1H-pyrazol-3-yl)-7-(2-methoxyethoxy)quinazolin-4-amine (230 mg, 0.531 mmol, 73.2% yield) as a yellow solid. $^1$H NMR (400 MHz, DMSO-d6) δ ppm 12.19 (s, 1H), 10.36 (s, 1H), 8.99 (s, 1H), 8.45 (s, 1H), 7.34 (s, 1H), 4.26-4.42 (m, 2H), 3.73 (t, J=4.4 Hz, 2H), 3.34 (s, 3H), 2.18 (s, 3H), 1.74 (s, 3H), 1.33 (s, 9H). MS (m/z) 434.

Example 2

6-(tert-Butylsulfonyl)-N-(4,5-dimethyl-1H-pyrazol-3-yl)-7-ethoxyquinazolin-4-amine

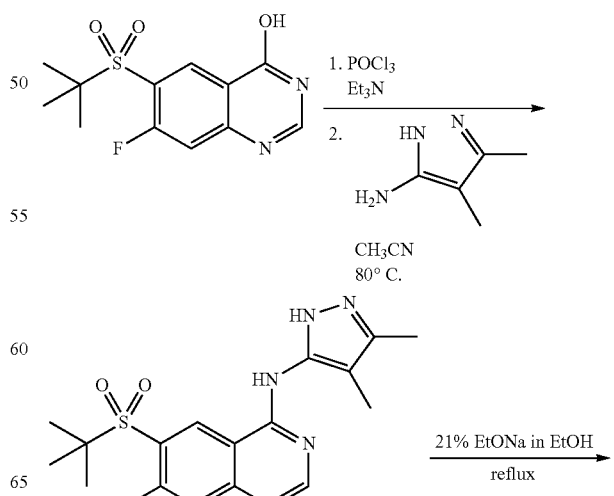

-continued

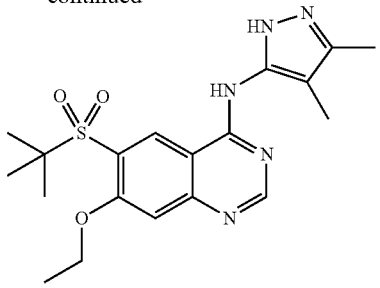

Step 1: 6-(tert-butylsulfonyl)-N-(4,5-dimethyl-1H-pyrazol-3-yl)-7-fluoroquinazolin-4-amine: To a suspension of 6-(tert-butylsulfonyl)-7-fluoroquinazolin-4-ol (5.50 g, 19.35 mmol) in acetonitrile (48 ml) was added POCl$_3$ (2.70 ml, 29.0 mmol) and TEA (4.0 ml, 29 mmol). The reaction mixture was stirred at 80° C. overnight. 4,5-Dimethyl-1H-pyrazol-3-amine (2.58 g, 23.2 mmol) was added to the solution, and reaction mixture continued to stir at 80° C. for 1 h. A solid started to precipitate out. The reaction mixture was allowed to cool to room temperature. Filtered solid and washed with cold acetonitrile. The solid was dried in a vacuum oven to provide 6-(tert-butylsulfonyl)-N-(4,5-dimethyl-1H-pyrazol-3-yl)-7-fluoroquinazolin-4-amine, hydrochloride (4.91 g, 11.86 mmol, 61.3% yield). (M+H)+378.2.

Step 2: 6-(tert-butylsulfonyl)-N-(4,5-dimethyl-1H-pyrazol-3-yl)-7-ethoxyquinazolin-4-amine: Sodium ethoxide (24 ml, 65.6 mmol, 21% in EtOH) and 6-(tert-butylsulfonyl)-N-(4,5-dimethyl-1H-pyrazol-3-yl)-7-fluoroquinazolin-4-amine, hydrochloride (4.80 g, 11.60 mmol) were combined, and the suspension was heated at 80° C. for 2 hours. The reaction mixture was allowed to cool to room temperature. EtOH was evaporated, and the residue was dissolved in 25 ml of water. The solution was neutralized to pH~9 by adding 1N HCl. Light yellow solid precipitated out. The solid was filtered, washed with water and dried in a vacuum oven overnight to provide 6-(tert-butylsulfonyl)-N-(4,5-dimethyl-1H-pyrazol-3-yl)-7-ethoxyquinazolin-4-amine (3.90 g, 9.67 mmol, 83% yield). (M+H)$^+$ 404.1; $^1$H NMR (DMSO-d$_6$, 400 MHz): δ=12.20 (s, 1H), 10.36 (s, 1H), 8.99 (s, 1H), 8.46 (s, 1H), 7.30 (s, 1H), 4.13-4.34 (m, 2H), 2.18 (s, 3H), 1.74 (s, 3H), 1.40 (t, J=6.9 Hz, 3H), 1.33 ppm (s, 9H).

A sample of 6-(tert-butylsulfonyl)-N-(4,5-dimethyl-1H-pyrazol-3-yl)-7-ethoxyquinazolin-4-amine (120 g) was suspended in EtOH (2000 ml), then heated to 70° C. Additional EtOH (2000 ml) was added and the resulting mixture was heated to reflux. Most of the solid dissolved in solvent. The hot suspension was filtered and the solution was poured into 12 L of cold water. This mixture was stirred for approximately 60 min, then allowed to sit overnight as the bath warmed to RT. A light yellow precipitate was isolated by filtration and dried in a vacuum oven to afford 105.9 g (261 mmol, 88% recovery) of crystalline 6-(tert-butylsulfonyl)-N-(4,5-dimethyl-1H-pyrazol-3-yl)-7-ethoxyquinazolin-4-amine, which is characterized by the PXRD pattern of FIG. 1 and the diffraction data in Table 1.

The PXRD analysis was conducted on a Rigaku Desktop X-ray Diffractometer, model Miniflex II, serial number DD02652 using a Scintillator NaI (TI) detector. The acquisition conditions included: Cu K$_\alpha$ radiation (λ=1.54059 Å), generator tension: 30 kV, generator current: 15 mA, start angle: 3.0° 2θ, end angle: 40.0° 2θ, step size: 0.04° 2θ, time per step: 0.5 seconds. The sample was prepared using zero background (front fill) technique.

TABLE 1

| Diffraction Angle (°2θ) | d-spacing [Å] | Relative Intensity [%] |
|---|---|---|
| 8.49 | 0.118 | 26.2 |
| 9.35 | 0.157 | 14.2 |
| 9.84 | 0.118 | 27.0 |
| 11.03 | 0.157 | 9.2 |
| 12.26 | 0.118 | 4.3 |
| 12.87 | 0.157 | 14.9 |
| 14.18 | 0.157 | 14.7 |
| 15.47 | 0.157 | 3.7 |
| 16.95 | 0.157 | 100.0 |
| 17.33 | 0.157 | 14.8 |
| 17.75 | 0.157 | 5.4 |
| 18.24 | 0.197 | 12.0 |
| 18.61 | 0.157 | 6.2 |
| 19.51 | 0.157 | 7.7 |
| 20.03 | 0.118 | 3.9 |
| 21.17 | 0.157 | 10.4 |
| 21.93 | 0.197 | 17.6 |
| 22.59 | 0.157 | 6.8 |
| 22.96 | 0.157 | 8.0 |
| 23.95 | 0.197 | 6.2 |
| 25.83 | 0.157 | 2.3 |
| 26.57 | 0.118 | 5.1 |
| 28.05 | 0.157 | 16.6 |
| 28.97 | 0.157 | 7.1 |
| 30.51 | 0.157 | 7.7 |
| 31.17 | 0.157 | 2.3 |
| 32.81 | 0.197 | 2.7 |
| 33.38 | 0.236 | 2.6 |
| 34.36 | 0.236 | 1.1 |
| 36.25 | 0.236 | 1.9 |
| 36.90 | 0.236 | 1.6 |
| 38.71 | 0.197 | 2.3 |

Example 3

6-(tert-Butyl sulfonyl)-N-(4,5-dimethyl-1H-pyrazol-3-yl)-7-propoxyquinazolin-4-amine

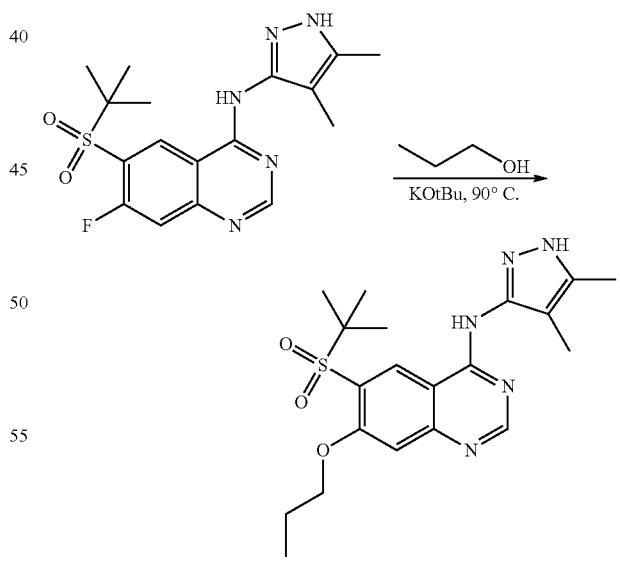

A mixture of 6-(tert-butylsulfonyl)-N-(4,5-dimethyl-1H-pyrazol-3-yl)-'7-fluoroquinazolin-4-amine (1.5 g, 3.97 mmol), propan-1-ol (17.85 ml, 238 mmol) and KOtBu (2.230 g, 19.87 mmol) was heated at 90 C for 21 h. The reaction was poured into ether—solution turned cloudy—no precipitate. The mixture neutralized with citric acid and extracted with EtOAc (1×) and 2-MeTHF (1×). The combined organics were washed with brine, dried over Na$_2$SO$_4$ and concentrated to dryness to afford crude product that was purified via HPLC (10-50% ACN/water, 0.1% TFA). The product-containing fractions were partitioned between EtOAc and sat. sodium bicarbonate, washed with brine, dried over Na$_2$SO$_4$ and concentrated to dryness. The resulting residue was triturated with EtOAc and filtered to afford 6-(tert-butylsulfonyl)-N-(4,5-dimethyl-1H-pyrazol-3-yl)-7-propoxyquinazolin-4-amine (280 mg, 0.671 mmol, 16.87% yield) as a white solid. $^1$H NMR (400 MHz, DMSO-d$_6$) δ ppm 12.19 (s, 1H) 10.36 (s, 1H) 8.99 (s, 1H) 8.45 (s, 1H) 7.29 (s, 1H) 4.17 (t, J=6.19 Hz, 2H) 2.18 (s, 3H) 1.76-1.84 (m, 2H) 1.74 (s, 3H) 1.26-1.37 (m, 9H) 1.07 (t, J=7.45 Hz, 3H). MS (m/z) 418.3 (M+H)+

Example 4

6-(tert-Butylsulfonyl)-N-(4,5-dimethyl-1H-pyrazol-3-yl)-7-((tetrahydrofuran-2-yl)methoxy)quinazolin-4-amine

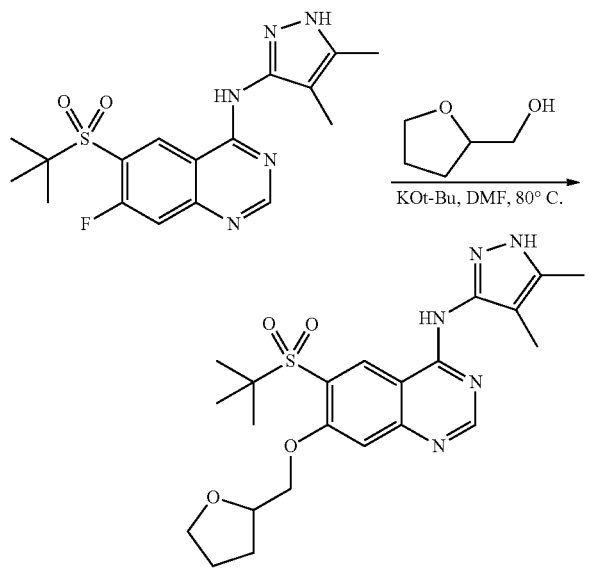

To a solution of (tetrahydrofuran-2-yl)methanol (148 mg, 1.45 mmol) in DMF (1 mL) was added KOtBu (163 mg, 1.45 mmol). The solution was stirred at room temp for 5 min. 6-(tert-butyl sulfonyl)-7-chloro-N-(4,5-dimethyl-1H pyrazol-3-yl) quinazolin-4-amine (30 mg, 0.076 mmol) was then added and the reaction mixture was stirred at 80° C. overnight. Most of the DMF was removed in vacuo. The crude material was purified by a biotage column (0 to 16% MeOH/DCM) to provide 6-(tert-butylsulfonyl)-N-(4,5-dimethyl-1H-pyrazol-3-yl)-7-((tetrahydrofuran-2-yl)methoxy) quinazolin-4-amine (40 mg, 0.084 mmol, 35% yield). $^1$H NMR (DMSO-d6) δ: 12.19 (br. s., 1H), 10.36 (br. s., 1H), 8.99 (s, 1H), 8.45 (s, 1H), 7.34 (s, 1H), 4.21 (m, 3H), 3.77-3.87 (m, 1H), 3.65-3.76 (m, 1H), 2.18 (s, 3H), 2.00 (m, 2H), 1.79-1.90 (m, 2H), 1.75 (s, 3H), 1.32 (s, 9H). MS (m/z) 460.

Pharmaceutical Compositions

Example A

Tablets are prepared using conventional methods and are formulated as follows:

| Ingredient | Amount per tablet |
| --- | --- |
| Compound | 5 mg |
| Microcrystalline cellulose | 100 mg |
| Lactose | 100 mg |
| Sodium starch glycollate | 30 mg |
| Magnesium stearate | 2 mg |
| Total | 237 mg |

Example B

Capsules are prepared using conventional methods and are formulated as follows:

| Ingredient | Amount per tablet |
| --- | --- |
| Compound | 15 mg |
| Dried starch | 178 mg |
| Magnesium stearate | 2 mg |
| Total | 195 mg |

Biological Assay:

A fluorescent polarization based binding assay was developed to quantitate interaction of novel test compounds at the ATP binding pocket of RIPK2, by competition with a fluorescently labeled ATP competitive ligand. Full length FLAG His tagged RIPK2 was purified from a Baculovirus expression system and was used at a final assay concentration of twice the KDapparent. A fluorescent labeled ligand (5-({[2-({[3-({4-[(5-hydroxy-2-methylphenyl)amino]-2-pyrimidinyl}amino)phenyl]carbonyl}amino)ethyl] amino}carbonyl)-2-(6-hydroxy-3-oxo-3H-xanthen-9-yl) benzoic acid, prepared as described in WO2011/120025) was used at a final assay concentration of 5 nM. Both the enzyme and ligand were prepared in solutions in 50 mM HEPES pH7.5, 150 mM NaCl, 10 mM MgCl$_2$, 1 mM DTT, and 1 mM CHAPS. Test compounds were prepared in 100% DMSO and 100 nL was dispensed to individual wells of a multiwell plate. Next, 5 ul RIPK2 was added to the test compounds at twice the final assay concentration, and incubated at rt for 10 min. Following the incubation, 5 ul of the fluorescent labeled ligand solution, was added to each reaction, at twice the final assay concentration, and incubated at rt for at least 10 min. Finally, samples were read on an instrument capable of measuring fluorescent polarization. Test compound inhibition was expressed as percent (%) inhibition of internal assay controls.

For concentration/dose response experiments, normalized data were fit and pIC$_{50}$s determined using conventional techniques. The pIC$_{50}$s are averaged to determine a mean value, for a minimum of 2 experiments.

| Example No. | pIC$_{50}$ |
| --- | --- |
| 1 | 7.4 |
| 2 | 7.8 |
| 3 | 7.9 |
| 4 | 8.0 |

Continued testing resulted in a slight change in the reported average pIC$_{50}$ for the compound of Example 1 (7.5) and Example 3 (8.1).

FLAG his Tagged RIPK2 Preparation:

Full-length human RIPK2 (receptor-interacting serine-threonine kinase 2) cDNA was purchased from Invitrogen (Carlsbad, Calif., USA, Clone ID:IOH6368, RIPK2-pENTR 221). Gateway® LR cloning was used to site-specifically recombine RIPK2 downstream to an N-terminal FLAG-6His contained within the destination vector pDEST8-FLAG-His6 according to the protocol described by Invitrogen. Transfection into *Spodoptera frugiperda* (Sf9) insect cells was performed using Cellfectin® (Invitrogen), according to the manufacturer's protocol.

Sf9 cells were grown in Excell 420 (SAFC Biosciences, Lenexa, Kans., US; Andover, Hampshire UK) growth media at 27° C., 80 rpm in shake flask until of a sufficient volume to inoculate a bioreactor. The cells were grown in a 50 liter working volume bioreactor (Applikon, Foster City, Calif., US; Schiedam, Netherlands) at 27° C., 30% dissolved oxygen and an agitation rate of 60-140 rpm until the required volume was achieved with a cell concentration of approximately $3.7 \times e6$ cells/mL. The insect cells were infected with Baculovirus at a multiplicity of infection (MOI) of 12.7. The cultivation was continued for a 43 hour expression phase. The infected cells were removed from the growth media by centrifugation at 2500 g using a Viafuge (Carr) continuous centrifuge at a flow rate of 80 liters/hour. The cell pellet was immediately frozen and subsequently supplied for purification.

Purification Procedure I: $9.83 \times 10^5$ Insectcells were re-suspended in 1.4 L lysis buffer (50 mM Tris (pH 8.0), 150 mM NaCl, 0.5 mM NaF, 0.1% Triton X-100, 1 mL/liter Protease Inhibitor Cocktail Set III (available from EMD Group; CalBiochem/Merck Biosciences, Gibbstown, N.J., US; Damstadt, Germany) and processed by dounce homogenization on ice. The suspension was then clarified by centrifugation at 47,900 g for 2 h, at 4° C. The lysate was decanted from the insoluble pellet and loaded at a linear flow rate of 16 cm/h onto a 55 mL FLAG-M2 affinity column ($2.6 \times 10.4$ cm) that had been pre-equilibrated with 10 column volumes buffer A (50 mM Tris (pH 8.0), 150 mM NaCl, 0.5 mM NaF, 1 mL/liter Protease Inhibitor Cocktail Set III). The column was then washed with 15 column volumes buffer A, and eluted with 6 column volumes buffer B (buffer A+150 µg/mL 3×FLAG peptide) at a linear flow rate of 57 cm/h. Fractions identified by SDS-PAGE as containing protein of interest were dialyzed to remove the 3×FLAG peptide from the preparation against 5 L of Buffer A (not containing the Protease Inhibitor Cocktail) overnight, using 10 kDa MWCO SnakeSkin Pleated Dialysis Tubing. The purification process yielded 11.3 mg of total protein, with the RIPK2 present at 40% purity by gel densitometry scanning, and identity confirmed by peptide mass fingerprinting. The main contaminating proteins in the preparation were identified as lower molecular weight degraded species of RIPK2.

Purification Procedure II: 100 g cells (10 liter scale fermentation) were frozen, thawed, and re-suspended in 1 L lysis buffer (50 mM Tris HCL pH7.5, 250 mM NaCl, 0.1 mM TCEP, 3 ml Protease inhibitor cocktail) and lysed by high pressure homogenization at 10,000 psi once (Avestin). The suspension was then clarified by centrifugation at 35,000 g for 45 minutes at 4° C. The supernatant was collected by centrifugation and incubated with 5 ml anti-FLAG-M2 resin which was pre-equilibrated with buffer A (50 mM Tris HCL pH7.5, 250 mM NaCl, 0.1 mM TCEP). After protein binding at 4° C. degree for 1 hour, the resin was packed into two 25 ml disposable columns. Each column was washed with 25 ml buffer A and eluted with 10 ml (buffer A+200 ug/ml Flag peptide). The elution pool was concentrated to 1 ml and applied to a superdex 200 (16/60) sizing column. Fractions containing full length RIPK2 were collected according to SDS-PAGE analysis results. The purification process yielded 1.36 mg/L 80% pure RIPK2 protein and identity was confirmed by peptide mass fingerprinting.

Biological Assay:

A muramyl dipeptide (MDP)-stimulated human whole blood cytokine production assay was developed to evaluate the cellular potency and efficacy of novel test compounds. Heparinized blood (160 µL) obtained from healthy human volunteers was dispensed into individual wells of a multi-well plate. Test compounds were dissolved in 100% DMSO and diluted in calcium- and magnesium-free D-PBS to prepare 10× working stock solutions. Twenty microliters of diluted test compound was added per well and the plates were placed on a plate shaker (500 rpm) and incubated for 30 min in a humidified incubator (37° C., 5% $CO_2$). A 10× working stock of MDP was prepared in sterile, endotoxin-free water containing 1% DMSO. Twenty microliters of the MDP stock solution was added per well (final conc.=100 ng/mL) to stimulate RIP2 kinase-dependent cytokine production. The final concentration of DMSO was 0.1% (v/v) in all wells. Plates were incubated for an additional 6 hr (as noted above). Then an additional 100 µL of D-PBS (Dulbecco's phosphate-buffered saline) was added/well, the plates were centrifuged, and supernatants collected. TNFα levels in the supernatants were quantified using a commercial immunoassay (MesoScale Discovery). Test compound inhibition was expressed as percent (%) inhibition of internal assay controls. For concentration/dose response experiments, normalized data were fit and $pIC_{50}$s determined using conventional techniques. The $pIC_{50}$s are averaged to determine a mean value, for a minimum of 2 experiments.

| Example No. | $pIC_{50}$ |
|---|---|
| 1 | 7.4 |
| 2 | 7.2 |
| 3 | 7.0 |
| 4 | 7.2 |

Biological In Vivo Assay—Inhibition of Induced Inflammatory Response

The efficacy of RIP2 inhibitors may also be evaluated in vivo in rodents. Intraperitoneal (i.p.) or intravenous (i.v.) administration of L18-MDP in mice has been shown to induce an inflammatory response through activation of the NOD2 signaling pathway (Rosenweig, H. L., et al. 2008. Journal of Leukocyte Biology 84:529-536). The level of the inflammatory response in the L18-MDP treated rats is monitored using conventional techniques by measuring increases in one or more cytokine levels (IL8, TNFα, IL6 and IL-1β) in serum and/or peritoneal lavage fluid and/or by measuring neutrophil influx into the peritoneal space (when L18-MDP is dosed i.p.). Inhibition of the L18-MDP induced inflammatory response in treated rats may be shown by orally pre-dosing with a test compound, then measuring and comparing one or more cytokine levels (IL8, TNFα, IL6 and IL-1β) in serum to control treated animals using conventional techniques.

Figure 2:
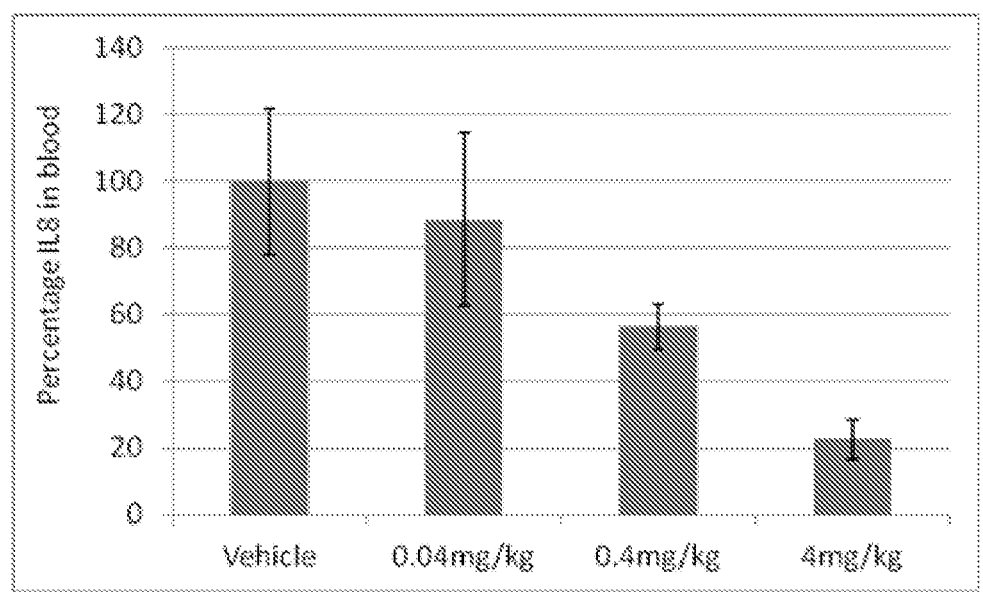
FIG. 2 shows the combined IL8 cytokine response in rat whole blood samples obtained after pre-dosing rats with the compound 6-(tert-butylsulfonyl)-N-(4,5-dimethyl-1H-pyrazol-3-yl)-7-ethoxyquinazolin-4-amine, followed by dosing with L18-MDP.

For example, rats were orally pre-dosed with the compound of Example 2, 6-(tert-butyl sulfonyl)-N-(4,5-dimethyl-1H-pyrazol-3-yl)-7-ethoxyquinazolin-4-amine, at doses of 0, 0.04, 0.4 and 4 mg/kg, followed by dosing with L18-MDP (50 μg/rat) 0.25 h/min after pre-dosing. IL8 cytokine levels in whole blood samples taken from the rats in this study were measured using antibody based detection (Meso-Scale Discovery platform). The IL8 cytokine response was calculated as the averaged response for each dose level expressed relative to the response observed in the vehicle-treated rats, and are depicted in FIG. 2 as the mean±standard error of the mean (n=8 rats/group).

Biological In Vivo Assay—Rabbit Cardiac Wedge Preparation

Female rabbits weighing 2.2-3 kg were anticoagulated with heparin and anesthetized with pentobarbital (50 mg/kg, i.v.). The chest was opened via a left thoracotomy, and the heart was excised and placed in a cardioplegic solution consisting of cold (4° C.) normal Tyrode's solution. A transmural wedge with dimensions of approximately 1.5 cm wide and 2-3 cm long was dissected from the left ventricle.

The wedge tissue was cannulated via the left anterior descending artery or the circumflex artery and perfused with cardioplegic solution. The preparation was then placed in a small tissue bath and arterially perfused with Tyrode's solution (T: 35.7±0.1° C., perfusion pressure: 30-45 mmHg). The ventricular wedge was allowed to equilibrate in the tissue bath until electrically stable, usually one hour. The preparations were stimulated at basic cycle lengths (BCL) of 1000 and 2000 msec using bipolar silver electrodes insulated except at the tips and applied to the endocardial surface.

A transmural electrocardiogram (ECG) was recorded in all experiments using extracellular silver/silver chloride electrodes placed in the Tyrode's solution bathing the preparation 1.0 to 1.5 cm from the epicardial and endocardial surfaces, along the same vector as the transmembrane recordings (Epi: "+" pole). On the ECG, transmural dispersion of repolarization (TDR) was defined by the interval between the end and the peak of T wave ($T_{p-e}$). The QT interval was defined as the time from the onset of the QRS to the point at which the final downslope of the T wave crossed the isoelectric line. QRS, QT, and Tp-e durations are measured for 10 sweeps and averaged per treatment. Data from total population of animals is averaged per treatment, and compared to average control values.

isometric contractile force generation (% ICF) is measured for 10 sweeps and averaged per treatment. Data from total population of animals is averaged per treatment, and compared to average control values.

Each test compound was prepared in 100% DMSO at a stock concentration of 30 mM. Compound was diluted to the highest concentration tested into Tyrode's buffer (containing in mM: 129 NaCl, 4 KCl, 0.9 $NaH_2PO_4$, 20 $NaHCO_3$, 1.8 $CaCl_2$, 0.5 $MgSO_4$, and 5.5 glucose, pH 7.4 when buffered with 95% $O_2$ and 5% $CO_2$) from which subsequent serial dilutions were prepared.

Each test compound was tested at 4 concentrations, from 1-30 μM. After the wedge preparations were perfused with normal Tyrode's solution and stimulated at a BCL of 1000 msec for one hour, stimulation frequency was reduced to a BCL of 2000 msec for a 5 minute period of stabilization after which baseline ECG and isometric contractile force (ICF) were recorded. The preparations were then returned to a BCL of 1000 msec and perfused with Tyrode's solution containing a test compound. For each test compound concentration, wedge preparations were perfused for 20 minutes at a BCL of 1000 msec followed by 5 minutes at a BCL of 2000 msec during which ECG and ICF were recorded. The compound of Example 2 (6-(tert-butylsulfonyl)-N-(4,5-dimethyl-1H-pyrazol-3-yl)-7-ethoxyquinazolin-4-amine) was evaluated in the rabbit cardiac wedge preparation. The four major readouts from the wedge preparation include QT prolongation, torsadogenicity (TdP score derived from QT, Tp-e and early after depolarizations), impulse conduction (QRS-related) and contractility, which are presented in Table 2.

A scoring system was used for the estimate of risk of a compound for the relative TdP risk using the isolated rabbit left ventricular wedge preparation: points for the QT interval, the $T_{p-e}$/QT ratio. The TdP score was generated by first converting the QT interval and Tp-e/QT ratio to % change from baseline. These values are individually assigned a TdP score based on the following system: <−5%=−1, −5% to 10%=0, 10% to 20%=1, 20% to 30%=2, >30%=3. Total scoring system range is −2 to 14 at BCL=2000 ms.

TABLE 2

Summary data (mean, n = 2).

|  | Control | 1 μM | 3 μM | 10 μM | 30 μM |
| --- | --- | --- | --- | --- | --- |
| QT (msec) | 335.5 | 346.4 | 351.9 | 348.8 | 348.8 |
| Δ QT % |  | 3 | 4.8 | 4.0 | 4.0 |
| Tp-e (msec) | 70.8 | 71.9 | 73.2 | 68.4 | 69.1 |
| QRS (msec) | 40.1 | 39.6 | 39.2 | 39.4 | 39.7 |
| ICF (% change) |  | −4.4 | −5.3 | −15.1 | −20.7 |
| Proarrhythmia | 0/2 | 0/2 | 0/2 | 0/2 | 0/2 |
| TdP Score | 0 | −0.50 | 0.00 | −0.50 | −0.50 |

QT = QT interval,
Tp-e = Transmural dispersion,
ICF = Contractility.

Kinome Selectivity

Kinome selectivity (as conducted by Reaction Biology Corporation, One Great Valley Parkway, Malvern, Pa., USA, 19355, http://www.reactionbiology.com) for the compound of Example 2 (6-(tert-butylsulfonyl)-N-(4,5-dimethyl-1H-pyrazol-3-yl)-7-ethoxyquinazolin-4-amine) was determined via in vitro profiling against a 337 member kinase panel. At a concentration of 1 μM, the compound of Example 2 demonstrated >70% inhibition of 1 of 337 kinases tested and >50% inhibition of 4 of 337 kinases tested.

References: WO2011/120025, WO2011/120026, WO2011/123609, WO2011/140442, WO2012/021580, WO2012/122011, WO2013/025958

What is claimed is:

1. A compound having the formula:

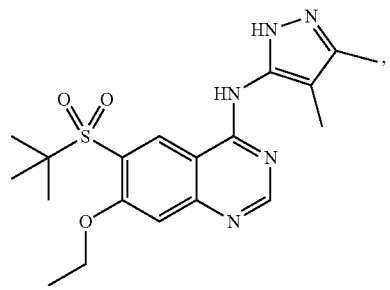

-continued

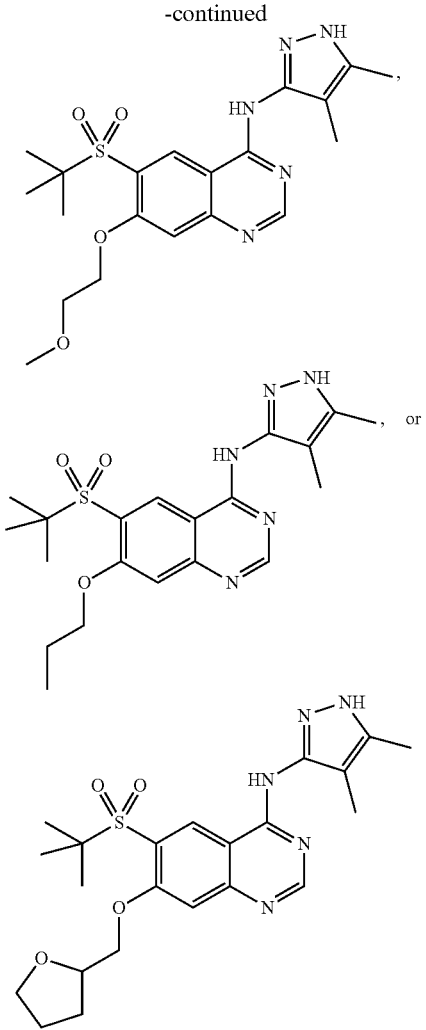

or a salt thereof.

2. A compound which is

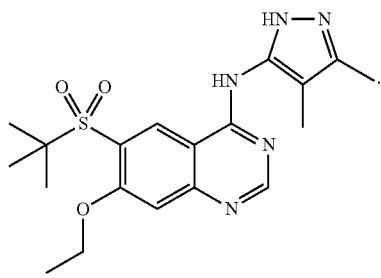 [SMILES: CCOc1cc2ncnc(Nc3[nH]nc(C)c3C)c2cc1S(=O)(=O)C(C)(C)C]

3. A compound which is

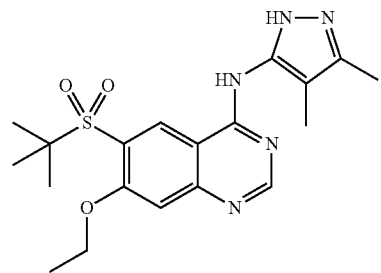 [SMILES: CCOc1cc2ncnc(Nc3[nH]nc(C)c3C)c2cc1S(=O)(=O)C(C)(C)C]

or a pharmaceutically acceptable salt thereof.

4. A pharmaceutical composition comprising the compound, or pharmaceutically acceptable salt thereof, according to claim 3 and one or more pharmaceutically acceptable excipients.

5. A pharmaceutical composition comprising the compound according to claim 2 and one or more pharmaceutically acceptable excipients.

6. A method of treating a RIP2 kinase-mediated disease or disorder which comprises administering a therapeutically effective amount of the compound, or pharmaceutically acceptable salt thereof, according to claim 3 to a human in need thereof, wherein the disease or disorder is selected from uveitis, dermatitis, acute lung injury, type 2 diabetes mellitus, arthritis, rheumatoid arthritis, ulcerative colitis, Crohn's disease, early-onset inflammatory bowel disease, extraintestinal inflammatory bowel disease, prevention of ischemia reperfusion injury in solid organ transplant, non-alcohol steatohepatitis, autoimmune hepatitis, asthma, systemic lupus erythematosus, multiple sclerosis, sarcoidosis, Blau syndrome, early-onset sarcoidosis, Wegner's granulomatosis, and interstitial pulmonary disease.

7. A method of treating a RIP2 kinase-mediated disease or disorder which comprises administering a therapeutically effective amount of the compound according to claim 2 to a human in need thereof, wherein the disease or disorder is selected from uveitis, dermatitis, acute lung injury, type 2 diabetes mellitus, arthritis, rheumatoid arthritis, ulcerative colitis, Crohn's disease, early-onset inflammatory bowel disease, extraintestinal inflammatory bowel disease, prevention of ischemia reperfusion injury in solid organ transplant, non-alcohol steatohepatitis, autoimmune hepatitis, asthma, systemic lupus erythematosus, multiple sclerosis, sarcoidosis, Blau syndrome, early-onset sarcoidosis, Wegner's granulomatosis, and interstitial pulmonary disease.

8. The method according to claim 6, wherein the disease or disorder is selected from uveitis, Blau Syndrome, early-onset sarcoidosis, ulcerative colitis, Crohn's disease, Wegener's granulamatosis and sarcoidosis.

9. The method according to claim 7, wherein the disease or disorder is selected from uveitis, Blau Syndrome, early-onset sarcoidosis, ulcerative colitis, Crohn's disease, Wegener's granulamatosis and sarcoidosis.

10. The method according to claim 6, wherein the disease is Crohn's disease.

11. The method according to claim 6, wherein the disease is ulcerative colitis.

12. The method according to claim 6, wherein the disease is Blau syndrome.

13. The method according to claim 6, wherein the disease is rheumatoid arthritis.

14. The method according to claim 7, wherein the disease is Crohn's disease.

15. The method according to claim 7, wherein the disease is ulcerative colitis.

16. The method according to claim 7, wherein the disease is Blau syndrome.

17. The method according to claim 7, wherein the disease is rheumatoid arthritis.

* * * * *